(12) United States Patent
Einerhand et al.

(10) Patent No.: US 6,232,105 B1
(45) Date of Patent: May 15, 2001

(54) CONDITIONAL REPLICATION AND EXPRESSION SYSTEM

(75) Inventors: Markus Peter Wilhelmus Einerhand, Amersterdam; Domenico Valerio, Leiden, both of (NL)

(73) Assignee: IntroGene B.V. (NL)

( * ) Notice: Subject to any disclaimer, the term of this patent is extended or adjusted under 35 U.S.C. 154(b) by 0 days.

(21) Appl. No.: 09/355,434

(22) PCT Filed: Jan. 29, 1998

(86) PCT No.: PCT/NL98/00061

§ 371 Date: Dec. 16, 1999

§ 102(e) Date: Dec. 16, 1999

(87) PCT Pub. No.: WO98/32870

PCT Pub. Date: Jul. 30, 1998

(30) Foreign Application Priority Data

Jan. 29, 1997 (EP) .................................................. 97200245

(51) Int. Cl.[7] .............................. C12P 19/34; C12N 5/00; C12N 15/63; C12N 15/85; C07H 21/04
(52) U.S. Cl. ..................... 435/91.4; 435/320.1; 435/325; 435/455; 536/23.1; 536/24.1
(58) Field of Search ................................ 435/91.4, 320.1, 435/325, 455; 536/23.1, 24.1

(56) References Cited

U.S. PATENT DOCUMENTS 5,658,776 * 8/1997 Flotte et al. ......................... 435/462

FOREIGN PATENT DOCUMENTS

WO 94/13788    6/1994  (WO).
WO 95/14771 *  6/1995  (WO).
WO 96/36364   11/1996  (WO).

OTHER PUBLICATIONS

Paper entitled "Cell Lines for the Production of Recombinant Adeno–Associated Virus"; K.R. Clark, F. Voulgaropoulou, D.M. Fraley and P.R. Johnson—Human Gene Therapy—Oct. 1995 vol. 6:1329–1341.

Paper entitled "A stable cell line carrying adenovirus–inducible rep and cap genes allows for invectivity titration of adeno–associated virus vectors"; K.R. Clark, F. Voulgaropoulou and P.R. Johnson—Gene Therapy (1996) vol. 3:1124–1132.

Paper entitled "Adeno–associated virus (AAV) vectors for gene transfer"; X. Xia, W. deVlaminck and J. Monahan—Advanced Drug Delivery Reviews (1993) vol. 12:201–215.

Wild et al. A broad–host–range in vivo pop–out and amplification system for generating large quantities of 50– to 100–kb genomic fragments for direct DNA sequencing. Gene. vol. 179:181–188 Oct. 1996.*

Posfai et al. In vivo ixcision and amplification of large segments of the *Escherichia coli* genome. Nuc. Acids. Res. vol. 22(12):2392–2398 Jun. 1994.*

Szybalski, W. From the double–helix to novel approaches to the sequencing of large genomes. Gene. vol. 135:279–290 Dec. 1993.*

* cited by examiner

*Primary Examiner*—Robert A. Schwartzman
*Assistant Examiner*—William Sandals
(74) *Attorney, Agent, or Firm*—Traskbritt

(57) ABSTRACT

The present invention relates to the utilization of conditionally replicating recombinant nucleic acid molecules rescued from the integrated state for the expression of foreign proteins. The usefulness of the system is illustrated with a conditionally replicating recombinant nucleic acid molecule encoding the adeno-associated virus (AAV) capsid proteins. The present invention also relates to methods employing and conditionally replicating recombinant nucleic acid molecules for the packaging of recombinant AAV nucleic acid molecule into AAV capsids. The present invention also relates to packaging cell lines for recombinant AAV, expressing both the AAV rep and cap-genes.

26 Claims, 21 Drawing Sheets

AAV-Genome Structure

Identified mRNA's and coding regions

\* ACG translation start of VP2

* not specific

Arrows indicate protein samples of clones reacting with the antiRep antibody 303.9

* not specific

SEQUENCE LISTING

<160> NUMBER OF SEQ ID NOS: 18

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Upstream
      primer

<400> SEQUENCE: 1
attaatctag actagtcgcg cagccgccat gccgggg                             37

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Downstream
      primer

<400> SEQUENCE: 2
tgtggaagta gctctctccc                                                20

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Upstream
      primer with additional sequence for restriction enzymes ClaI and
      AvrI

<400> SEQUENCE: 3
ggtatcgatc ctaggcgtca gacgcggaag cttcg                               35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Downstream
      primer  with additional sequence for restriction enzymes BglII and
      SpeI

<400> SEQUENCE: 4
ccaactagta gatctgcttc caccactgtc ttattc                              36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Sequence is
      sense oligo and is hybrizied to  anti-sense oligo to create linker

<400> SEQUENCE: 5
cggccgcctc ggccctctag agccttctta aggcga                              36

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Anti-sense
      oligo portion of linker

<400> SEQUENCE: 6
ctagtcgcct taagaaggct ctagagggcc gaggcggccg gtac                44

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Upstream
      primer with sequences for restriction enzymes KpnI, XbaI and SfiI

<400> SEQUENCE: 7
ggggtacctc tagagtcctg tattagaggt cacgtg                        36

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Downstream
      primer  with sequences for restriction enzymes KpnI, SpeI and SphI

<400> SEQUENCE: 8
ccggtaccac tagtacgcat gcttaaatac ccagcgtgac cac                43

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Upstream
      primer with sequences for restriction enzymes KpnI, SphI and SpeI
      that is used to carry out rep-gene amplification

<400> SEQUENCE: 9
ggggtaccgc atgcgtacta gtcgagggtc tccattttga agcgg              45

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Rep-specific downstream primer

<400> SEQUENCE: 10
aaccgtttac gctccgtgag                                          20

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Upstream
      primer

<400> SEQUENCE: 11
ataagaatgc ggccgctcgc cctcccagct aacaca                        36

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Downstream
      primer

```
<400> SEQUENCE: 12
agtttagcgg ccgcagatct tcgttcgaag gcctggacat gtccaggc          48

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: strand
      oligo

<400> SEQUENCE: 13
catggcggcc gcagatctc                                          19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Anti-strand
      oligo

<400> SEQUENCE: 14
catggagatc tgcggccgc                                          19

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Upstream
      primer with sequences for restriction enzymes BglII and NotI

<400> SEQUENCE: 15
ggacagatct gcggccgcac tcctttaagt gcgttacc                      38

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Downstream
      primer with a sequence for restriction enzyme BglII

<400> SEQUENCE: 16
ggaacagatc tgcgattctc ctaatggtct cc                            32

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 17
cacagatctg cggccgccag gggctgcagg tcgttac                       37

<210> SEQ ID NO 18
<211> LENGTH: 38
<212> TYPE: DNA
<213> ORGANISM: Artificial Sequence
```

```
<220> FEATURE:
<223> OTHER INFORMATION: Description of Artificial Sequence: Primer with
      BglII site

<400> SEQUENCE: 18
tggagatctg cggccgcccg ccacactcgc agggtctg                              38
```

CONDITIONAL REPLICATION AND EXPRESSION SYSTEM

TECHNICAL FIELD OF THE INVENTION

The present invention relates to the field of molecular biology, in particular the field of systems for the replication, transcription and/or expression (especially translation into protein) of genes or other nucleic acid molecules of interest.

BACKGROUND OF THE INVENTION

So many of these systems have been developed over the last two or three decades that it is hardly feasible to give a useful summary of the many possibilities. These possibilities are generally known to the people skilled in this art anyway. However, there are a number of genes which are difficult to replicate, transcribe or express for a variety of reasons. A quite obvious reason is for instance that the product produced upon expression is toxic to the cell in which the nucleic acid of interest is expressed. There are however less clear reasons why replication, transcription or expression of a nucleic acid of interest does not lead to useful levels of replication, transcription and/or expression. This invention typically deals with the replication, transcription and/or expression of such nucleic acids. The present invention was made during research involving adeno associated virus (AAV) and is typically useful for replication, transcription and/or expression of nucleic acids in an AAV-based system and typically for replication, transcription and/or expression of AAV-genes, in particular the cap-gene. However, other genes resisting replication, transcription and/or expression in the regular systems or genes or other nucleic acids that may only be produced upon induction will also be suitable for use in the presently invented system. The invention will however ne explained in more detail based on the AAV-system. AAV is a virus that is typically suggested for use in gene therapy, whereby a gene of interest is packaged into an AAV virion, which can infect a cell to be provided with said gene. The present invention arrives at a universal packaging system for AAV derived vectors provided with such a gene therapy related nucleic acid.

AAV is a non-pathogenic human parvovirus (reviewed in[1,2]). The virus replicates as a single strand DNA of approximately 4.6 kb. Both the plus and the minus strand are packaged and infectious. Efficient replication of AAV requires the co-infection of the cell by a helper virus such as Adenovirus or Herpes Simplex Virus. In the absence of a helper virus, no substantial replication of AAV is observed. AAV is therefore also classified as a "Dependovirus", When no helper virus is present, the AAV genome can integrate into the host cell genome. The wild-type virus has a strong preference (70%) for an integration site on the long arm of chromosome 19 (19 q13.3)[3-5]. Following integration, the expression of the virus genes is not detectable. The integrated provirus replicates as a normal part of the host cell genome upon division of the transduced cell and ends up in both daughter cells. This stage of the virus life cycle is known as the latent stage. This latent stage is stable but can be interrupted by infection of the transduced cell by a helper virus. Following infection of the helpervirus, AAV is excised from the host cell genome and starts to replicate. During the early phase of this lytic cycle the rep-genes are expressed. Approximately 12 to 16 hours later, the capsid proteins VP1, VP2 and VP3 are produced and the replicated virus DNA is packaged into virions (structure of the AAV-genome and its genes is depicted in FIG. 1). The virions accumulate in the nucleus of the cell and are released when the cell lyses as a result of the accumulation of AAV and the helpervirus (reviewed in[1,2]).

The AAV-genome contains two genes named rep and cap (FIG. 1). Three promoters (P5, P19 and P40) drive the synthesis of mRNAs coding for 4 Rep-proteins (Rep78, Rep68, Rep52 and Rep40) and three capsid proteins (VP1, VP2 and VP3). The AAV-genome is flanked on both sides by a 145 bp sequence, called the Inverted Terminal Repeat (ITR), which appears to contain all the cis-acting sequences required for virus integration, replication and encapsidation[6,7].

The capsid proteins VP1, VP2 and VP3 are produced from a 2.6 kb transcript of the AAV P40 promoter, which is spliced into two 2.3 kb mRNAs by using the same splice donor but two different splice acceptor sites. The splice acceptor sites are located at both sides of the VP1 translation start signal. VP1 is translated from the messenger that uses the splice acceptor directly in front of the VP1 translation initiation codon. VP2 and VP3 are translated from messengers that are spliced to the acceptor 3' of the VP1 ATG. VP2 and VP3 are translated from this messenger by use of an ACG translation start (VP2) or a downstream ATG (VP3). Since all three coding regions are in frame, the capsid proteins share a large domain with an identical amino-acid sequence. VP3 is entirely contained within VP1 and VP2, but the latter two contain additional amino-terminal sequences. Similarly, VP1 contains the entire VP2 protein but carries an additional N-terminal sequence. All three capsid proteins terminate at the same position[8]. The AAV capsid is 20 to 24 nm in diameter[9,10] and contains approximately 5% VP1, 5% VP2 and 90% VP3. This ratio is believed to reflect the relative abundance of the alternatively spliced messengers and the reduced translation initiation efficiency at the ACG initiation codon for VP2.

During a productive infection, the P5-promoter is activated first and directs the production of the large Rep-proteins, Rep78 and Rep68. These proteins are essential for AAV-replication and trans regulation of viral and cellular genes. The large Rep-proteins activate the P19 and the P40 promoter. In a latent infection, however, Rep78 and Rep68 down regulate expression of the P5 promoter and help to maintain the latency of AAV (for a review see[1]). The smaller Rep-proteins, Rep52 and Rep40, are encoded by transcripts from the P19 promoter and are important for the formation of infectious virus[11]. The P40 promoter is the last promoter to become activated and its activation follows the expression of the late genes of the helper adenovirus. Via alternative splicing, different mRNAs are produced coding for the structural proteins VP1, VP2 en VP3[12].

Adeno-Associated Virus Vector Technology

The first recombinant AAV vectors were made by replacing sequences from the rep or the cap gene by the sequences of interest[13-15]. Two methods were used to package the recombinant vector. In one method, the vector genome was packaged by co-transfecting into adenovirus infected cells a plasmid containing the vector together with a plasmid containing the missing AAV-gene. In the second method, a plasmid containing the vector was co-transfected with an AAV-genome that was too large to be packaged by an insertion of lambda phage DNA[13-15]. Recombinant virus produced in this way is always contaminated with wild-type AAV (ranging from 10–50% compared to the recombinant titer). This is presumably due to recombination between the two co-transfected plasmids which contain a substantial region of overlap, or by loss of the lambda DNA sequence. The contaminating wild-type AAV causes a further amplification of the rAAV upon infection of a new batch of adenovirus infected cells, leading to higher rAAV-titers but also leading to amplification of the contaminating wild-type AAV[13-15].

To circumvent the production of wild-type AAV, a packaging plasmid was constructed that contains no overlap with the vector plasmid[7]. With this packaging plasmid, it is possible to generate rAAV virus stocks that are free of detectable amounts of wild-type AAV, while at the same time it enables the production of 0.1 to 1 rAAV particles per cell[7]. This packaging system, or analogous systems derived therefrom, are currently used by most laboratories. Although this is the method of choice at this moment, the method is far from optimal since it cannot easily be scaled up to allow industrial production of rAAV vectors. Plasmid transfections are inherently inefficient and difficult to standardize or to scale up. This is even more true for co-transfections. In addition, whereas the wild-type virus replicates to $10^3$–$10^4$ particles per cell, the yield of rAAV in a typical rAAV-production is very low with the current methods (01–1 particles per cell)[7, 16]. This low yield makes purification of the rAAV a difficult task to undertake. The production problems pose a serious technological obstacle for the further development of AAV-vector technology for, for instance, gene therapy purposes. There is clearly a great need for an efficient and simple method for the production of rAAV. A very convenient packaging system would be in vitro packaging of rAAV by purified recombinantly produced AAV-proteins. A practical alternative is the generation of a packaging cell line for rAAV where the packaging cell line supplies in trans the required AAV and helper virus proteins for the production of rAAV. The specific recombinant AAV producing cell lines are then generated by stable transfection of a plasmid containing the recombinant AAV into the packaging cells. The present invention is useful for both the in vitro packaging strategy and the packaging cell line strategy.

Recombinant AAV Packaging Cell Lines

Packaging cell lines are currently the most efficient way in which retrovirus and adenovirus vectors are produced for industrial an/or therapeutic purposes such as gene therapy[17, 18]. Virus protein production for the in vitro packaging on an industrial scale is currently employed for Lambda phages, but not for other viruses. The generation of general packaging cell lines for rAAV has been an elusive goal for many years. Recombinant AAV packaging cell lines require that the in trans required AAV-proteins are only functional during the production phase of the rAAV vector. Constitutive function or expression is not desired for at least two reasons: 1) rescue and replication of the vector DNA prior to pro-duction would interfere with the growth and the stability of the cell line and 2) specifically the AAV-Rep-proteins are toxic to cells even in the absence of a recombinant AAV vector. The latter is largely due to the well documented, but as yet not explained, anti-proliferative effect of the large Rep proteins[19, 20]. Rep78 and Rep68 repress both cellular and viral promoters in transient assays[21, 22]. Upon stable transfection, the large Rep proteins inhibit cell proliferation[19, 20]. The mechanism is not well understood. It is possible that the observed inhibition of mRNA transcription and translation represses the production of crucial cellular gene-products[23, 25]. On the other hand, is it possible that the large Rep-proteins inhibit DNA replication directly[26, 22, 27]. Considering the pleiotropic effect of Rep-protein expression on cells, it is possible that both effects play a role in the anti-proliferative effect of the large Rep-proteins.

Cell Lines With Inducible Rep-Gene Expression

Until now, it has not been possible to make stable cell lines expressing the large Rep-proteins constitutively (see above). Following substitution of the P5 promoter with an inducible promoter, such as the methallothionine promoter[20] or the steroid inducible Mouse Mammary Tumor Virus (MMTV) long terminal repeat (LTR) promoter[19], it was possible to isolate out of a large number of clones, one and two clones that inducibly expressed Rep78, respectively. Rep52 was expressed constitutively in two of the three clones, whereas Rep68 and Rep40 which are translated from the spliced mRNAs, were not detectable[19, 20]. Although these clones were able to functionally produce Rep78 and Rep52, the levels were too low for the replication and packaging of recombinant AAV[19, 20]. Apart from this, the percentage of clones expressing Rep78 was low. Probably, there was a strong selection against a high level of rep expression. In case of the MMTV-promoter driven rep-expression, the replication and production of infectious virus of rep-negative recombinant AAV constructs could be improved by adding a construct constitutively expressing Rep40[28]. Still, at least three problems remain[19, 20, 28]: 1) The cell lines do not express capsid proteins. Capsid proteins need to be supplied through transfection of a capsid gene construct. 2) Significant replication of rAAV-constructs requires transfection of the glucocorticoid receptor (in case of the MMTV-promoter). 3) The yield of rAAV is not improved over the transient packaging systems and thus is not sufficient for industrial use in the sense of production of gene delivery vehicles.

Recently, we were able to generate cell lines with inducible and high level rep-gene expression using an improved inducible promoter system. However, also for these cell lines the capsid genes need to be added externally during virus production.

Recently, Clark et al. reported the generation of a full complementing cell line[29]. Although they do not know how to reconcile their results with the results of most other laboratories, they succeeded in generating cell lines inducibly expressing rep and cap from constructs that were stably integrated into the host cell genome. Unfortunately, this result was only obtained when the rep-gene, the cap-gene, a dominant selectable marker gene and the rAAV-vector sequences were present on the same plasmid, thus resulting in dedicated packaging cell lines. These packaging cells can, therefore, only be used for the production of the specific rAAV introduced together with the rep and cap genes and not be used to produce a different rAAV vector. It was also attempted to generate a general packaging cell line[29]. A cell line was obtained that inducibly replicated introduced rAAV and expressed the cap-gene. However, the levels of rep-expression where significantly lower than in the dedicated cell lines and although cap-RNA was produced, the levels were insufficient to make this cell line suitable for packaging of recombinant AAV. Since the rep and the cap-genes are physically linked to each other in this approach, it is not likely that the levels of rep and cap can easily be enhanced. For instance, there is the risk that rep-gene expression in the uninduced state is elevated to a level toxic for the packaging cells. This cell line was intended for and is useful for determining the infectious titer of rAAV preparations and testing of new rAAV vectors in a transient assay[29, 30].

SUMMARY OF THE INVENTION

The present invention provides a system for conditionally replicating, transcribing and/or expressing recombinant nucleic acid molecules that can be used to obtain very high expression of a foreign gene. Said system is specifically suited for the expression of genes that are not expressed efficiently by traditional polymerase II promoters, from non-replicated DNA or from chromosomally integrated foreign DNA. In addition, such a system is suited for the generation of cell lines stably transformed with the gene of interest, which only upon induction of replication will express significant amounts of product encoded by said foreign gene.

Thus, the invention provides a method for conditional replication of a nucleic acid of interest which nucleic acid is present, integrated in the genome of a eukaryotic host cell, comprising providing said nucleic acid with at least one regulatory element which essentially represses replication in an integrated setting, but allows replication in an episomal setting, further providing said nucleic acid with at least a means for functionally excising said nucleic acid in a functional form upon the presence of a signal, whereby said resulting nucleic acid in episomal functional form is replicated.

As used herein, essentially repressed means that no replication, transcription or expression of the nucleic acid occurs to any significant extent in the sense that it can be used for production of said sequence or a product thereof. At least replication will occur when the genome of the host is replicated, but even some additional replication, transcription and/or expression may occur.

As used herein, functionally excising means that the sequence of interest may be physically excised from the genome, i.e. become episomal, but also that the sequence can be functionally separated from the rest of the genome in the sense that it replicates, is transcribed and/or expressed separately from the genome and that the real functional replication, transcription and/or expression, only occurs using episomal copies of the sequence of interest.

As used herein, a signal means any means which is capable of inducing functional excision of the sequence of interest. In the case of AAV based systems, this may be the presence of Rep-proteins, in particular Rep68 or Rep78 or a functional fragment or derivative thereof (functional in this case meaning capable of inducing replication of the AAV vector's replication) which induces expression of the cap-gene, or any gene that has been placed under the control of cap-gene regulatory elements. In the latter embodiment, any gene, or DNA-molecule for that matter, can be replicated, transcribed and/or expressed upon induction by Rep-proteins. In the earlier embodiment, where Cap-proteins are expressed upon induction, a packaging cell line for AAV based vectors is provided, thus enabling the production at significant levels of AAV based gene delivery vehicles, which are thus also a part of the present invention, when obtainable by using, for instance, a packaging cell line according to the invention. A gene delivery vehicle is defined herein as an AAV-like virus particle, comprising a nucleic acid molecule based on an AAV-derived vector (having at least a functional AAV-packaging signal), which nucleic acid molecule comprises a sequence of interest to be delivered to a cell to be infected by said gene delivery vehicle, especially in the context of gene therapy. A sequence of interest may be a sequence encoding a protein or, for instance, a sequence encoding an antisense RNA or DNA molecule.

It is preferred, according to the present invention, to use a means for functionally excising a nucleic acid of interest from the genome which is based upon a viral replication system. These systems are explained in more detail herein. One such a preferred system is the presence of two AAV-ITR's on either side of the nucleic acid or DNA molecule of interest. Another preferred system is a system whereby the excision means is derived from a papova virus, preferably a polyoma virus, particularly SV40.

In the first embodiment, the signal for excision is the earlier discussed presence of Rep-proteins; in the second embodiment, the signal is the so-called large T-antigen or a functional fragment or derivative thereof. As a secondary level of control, it is preferred to place the excised sequence under control of an inducible promoter. This leads to clear advantages, for instance, because transcription and translation can be induced after a time interval of sufficient length to allow for a large number of copies of the sequence of interest to have been replicated. In the production of a packaging system, it is preferred that the nucleic acid of interest comprises at least a functional part or derivative of a cap-gene of Adeno Associated Virus (AAV). In this case, functional means that the protein must be capable of partaking in the packaging of an AAV-based vector.

The invention further provides a recombinant vector for carrying out a method, according to the invention, comprising a nucleic acid sequence of interest, a means for integration into the genome of a eukaryotic host cell, a means for functional excision of the nucleic acid of interest after integration upon the presence of a signal, a means for essentially repressing replication of said nucleic acid of interest in the integrated format and a means for allowing replication of the nucleic acid of interest in the episomal format, whereby one or more of the mentioned means may be one and the same. Preferably, such a vector is one whereby at least one of the mentioned elements is derived from AAV, or one whereby at least one of the elements is derived from a papovavirus, preferably a polyomavirus, in particular SV40.

The essential elements for a vector derived from AAV are: when a packaging cell line is to be produced, the AAV-ITR's and a functional, cap-gene, whereby functional has been defined hereinbefore.

For a papova based vector an SV40 origin of replication is essential.

Of course, for these vectors, it is again preferred that the sequence of interest is placed under the control of an inducible promoter. The invention also provides a recombinant eukaryotic host cell comprising a vector according the invention, preferably a cell further comprising a vector encoding at least a functional part of a rep-gene of AAV. This, of course, is a packaging cell for AAV-based vectors, which, preferably, comprises all AAV genes in trans which are deleted from the recombinant AAV derived vector.

In a further preferred embodiment, the conditionally replicating nucleic acid molecule is stably integrated in the host cell genome, while the DNA encoding a protein or proteins governing the specific replication of said nucleic acid molecule is introduced at the time replication is desired.

In yet another preferred embodiment of the invention, said nucleic acid molecule is stably integrated in the host cell genome, while the DNA encoding a protein or proteins governing the specific replication of said nucleic acid molecule is also stably integrated in the host cell genome. In the latter case, the DNA encoding said protein or proteins is expressed conditionally. Alternatively, said protein or proteins are engineered in such a way that its replicative functions are in-operative until induced. This can be achieved, for instance, by generating temperature sensitive mutants or by generating chimeric proteins from which the activity or compartmentalization in the cell can be regulated.

In another preferred embodiment of the invention, said nucleic acid molecule comprises the SV40-origin of replication while said protein is SV40 Large T-antigen. As stated hereinbefore, in one particularly preferred embodiment, said nucleic acid molecule contains two SV40 origins of replication, preferably flanking said foreign gene and positioned in the same orientation on said nucleic acid molecule so as to enable a polymerase chain reaction-like amplification of the internal sequences.

In another preferred embodiment, the invention provides a method for the generation of conditionally replicating molecules.

In another embodiment, the invention provides a stable cell line expressing AAV-2 capsid proteins VP1, VP2 and VP3 in a regulated fashion. The relative ratio of VP1, VP2 and VP3 and the absolute quantity of capsid protein in the cell approximate the expression of capsid proteins in wtAAV-2—infected cells. The amount of capsid protein in the cell and the relative ratio of the capsid proteins VP1, VP2 and VP3 enable the production of AAV-capsids and allows for the efficient packaging of modified wild type and recombinant AAV genomes. A cell line, according to this embodiment of the invention, is useful for the generation of a recombinant packaging cell line conditionally expressing both the AAV-rep gene and the AAV-cap gene. Moreover, said cell line is useful for the production and purification of AAV-capsid proteins and intact AAV-capsids useful for the in vitro packaging of foreign DNA or incorporation into virosomes.

In yet another earlier discussed embodiment, the invention provides a procedure for the generation of a fully complementing general rAAV-packaging cell line. A large variety of recombinant AAV vectors can be produced by their introduction into said packaging cell line followed by the induction of the lytic cycle. The recombinant AAV DNA can be introduced by means of transfection or infection into the packaging cells for each production or a stable cell line can be created carrying the recombinant AAV DNA stably integrated in the DNA of the packaging cell. In the latter case, production of recombinant AAV can proceed upon induction of the packaging functions and infection with a helper virus such as adenovirus. This system offers the advantage that the cell line can be grown to high cell numbers prior to the production of rAAV, a desirable feature for large scale production purposes. Using the procedure according to this embodiment of the invention, the production process is simplified significantly due to the reduction of components and manipulations that need to be carried out for each production run. It also allows for consistent production since the cell line can be analyzed and tested for undesirable contaminations and production features. In addition, it enables the standardization of the production process, since it avoids DNA introduction into cells via transfection procedures. The manipulations required are easy to scale up (i.e. induction of rep and cap gene expression by changing the cells environment (i.e. the medium) and the infection with a helpervirus such as adenovirus). A cell line generated according to the procedure of the present invention has the special feature of regulating the AAV-gene expression such that it reflects the expression of AAV-genes in a normal lytic cycle of wtAAV (i.e. early and late expression of rep and late expression of cap). It is another aspect of the invention that it provides a method for the drastic reduction of wtAAV formation during the production of recombinant AAV. Although the problem of wtAAV-formation was reduced by the invention of Samulski et al[7], recombinant AAV preparations still are often contaminated with wtAAV. Samulski et al removed most of the sequence overlap between the packaging construct and the recombinant AAV construct leaving only the 6 bp overlap of the XbaI site. The formation of wtAAV in this system is either dependent on homologous recombination events between the packaging and the recombinant AAV construct using the 6 bp overlap, or due to non-homologous recombination since there are extremely large amounts of DNA formed during a productive cycle. The reduction of overlap alone necessitates two recombination events between the packaging and the recombinant AAV construct before wtAAV is formed. We also follow a strategy that relies on minimizing the region of overlap. However, the present invention provides a system in which it is possible for the first time to separate the rep and the cap-gene constructs. By physically separating the transcription units of rep and cap they can be introduced at different positions in the host cell chromosome without loss of 1) expression levels and 2) the regulated and timed expression of rep and cap in the early and late phase of the lytic cycle. The physical separation of the transcription units of rep and cap introduces an extra obstacle for the formation of WtAAV since now three recombination events are required for the formation of wtAAV. In addition, the separation of the transcripts allows for the reduction of the amount of AAV DNA in the cell since now only the cap-gene DNA accumulates to large amounts in the cell. The rep-specific DNA is present in a low number of copies in the cell and thus forms an inefficient target for the recombination process.

As used herein, the term "gene" refers to a nucleic acid molecule encoding a protein and/or RNA.

As used herein, the term "wtAAV" refers to a nucleic acid molecule containing the genes rep and cap derived from AAV serotypes 1, 2, 3, 4 or 5 or functional analogs or parts thereof physically linked to two AAV-ITR.

As used herein, the term "recombinant AAV vector" means a nucleic acid molecule comprising at each end an AAV-ITR. When packaging into AAV-virions is desired, the size of the recombinant AAV vector is limited by the size constraints for packaging into AAV particles, which with the current state of the technology is about 5 kb. The recombinant AAV vector, preferably, does not contain sequences functionally analogous to the terminal resolution site in the AAV-ITR, as this might interfere with the stability of the recombinant vector. The recombinant AAV vector can contain any sequence, however, preferably, it contains a gene with therapeutic properties when introduced into cells of a patient. The gene can be therapeutic directly but, preferably, encodes for one or more proteins or RNA with therapeutic properties. Non-limiting examples of such genes are the human lysosomal glucocerebrosidase gene (E.C.3.2.1.45); a globin gene from the human b-globin gene cluster physically linked to sequences from the b-globin locus control region; a gene encoding an RNA or protein with anti-viral activity and the human multidrug resistance gene 1 (MDR1).

It will be understood that by the term "recombinant AAV packaging cell" is meant a cell line that provides in trans the required AAV-proteins necessary for the replication and/or packaging of modified wild-type or recombinant AAV genomes. The in trans required proteins are provided either in a constitutive fashion or in a regulated fashion.

As used herein, the term "functional levels of parvovirus protein expression" refers to levels of expression sufficient for replication and/or packaging of recombinant or modified wild-type parvovirus genomes.

As used herein, the term "replication", with respect to viral DNA, refers to a process of multiplication of a nucleic acid molecule distinct from the normal replication of eukaryotic chromosomal DNA, in that not just one but, indeed, many copies of the replicating molecules are formed in a cell during the process.

As used herein, the term "replicating DNA molecule" refers to a DNA molecule which can undergo replication in a cell. The replication can start from an integrated DNA molecule or from a DNA molecule that is present in the nucleus of a cell as an episome.

It is understood that by the term "regulated expression" is meant expression levels that can be altered by either manipulating the cells environment, for instance, but not limited to, the addition/removal of compounds to/from the medium in which the cells are grown, or by transfecting into cells DNA, RNA or protein or by infecting the cells with a virus such as adenovirus or herpes simplex virus.

It will be further understood that by the term "regulated promoter" is meant a nucleic acid molecule, that enables the regulated expression of a linked gene.

As used herein, the term "conditionally replicating DNA molecule" refers to a replicating DNA molecule from which the level of replication can be modified by the function of a protein or proteins of which the expression can be regulated.

Panel B shows an overnight exposure of the same DNA as in panel A, but it is now hybridized with a rep-specific probe.

Figure 20:
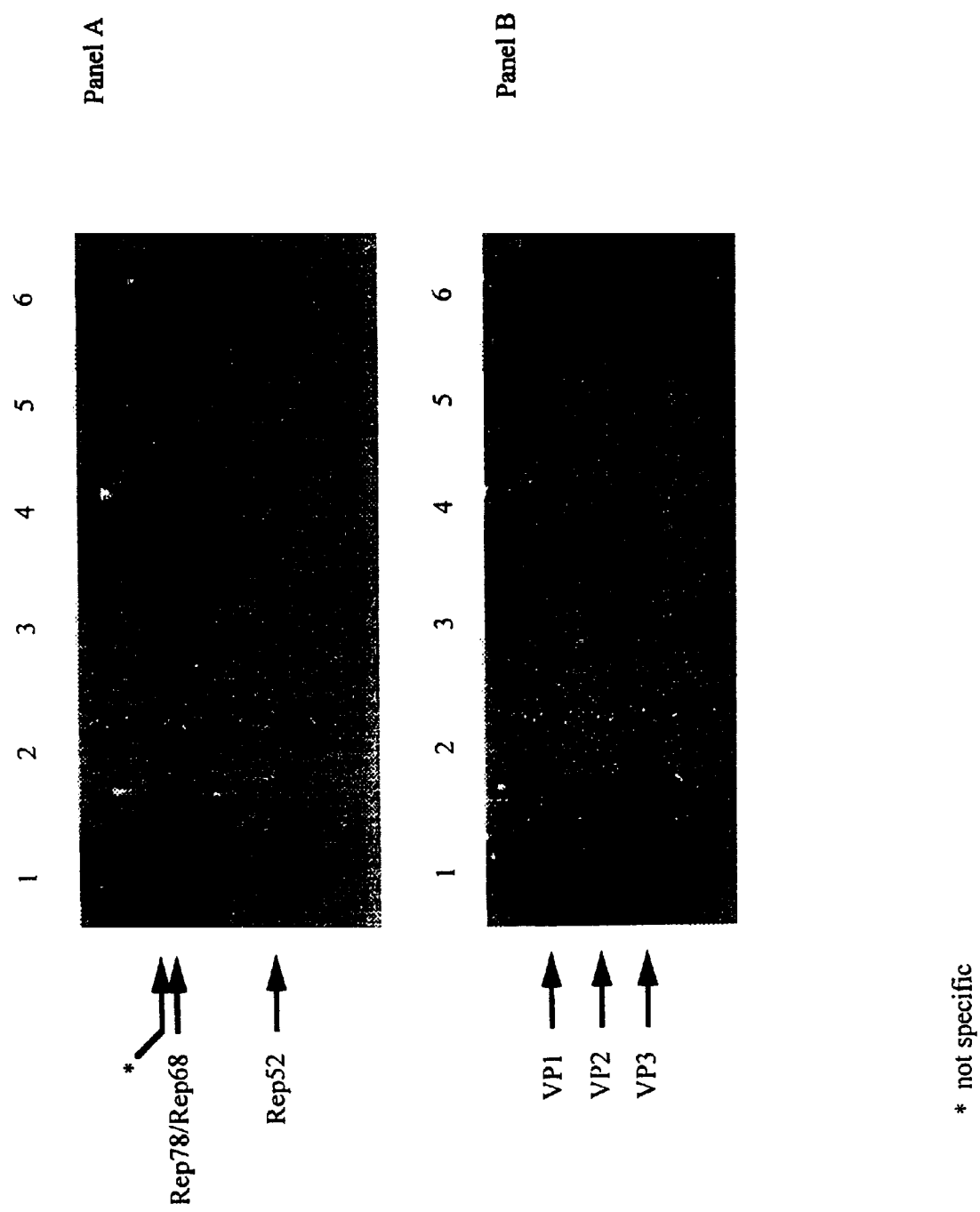

FIG. 20 shows an AAV-protein expression in CARE.1 cells CARE.1 cells were seeded in medium without doxycyline and either infected (lane 6) or not infected (lane 5) with adenovirus. After 48 hours, protein was extracted and Western blotted. Rep-proteins were visualized with antibody 303.9. A cross-reacting a-specific band is detected with this batch of antibody (*). Capsid proteins were visualized with antibody B1. Lane 1 shows protein harvested 48 hours after transfection of a transient transfection of pITR6.5cap and ptet*p5repEcoNI into adenovirus infected HtTA cells. Lane 2 shows protein from adenovirus infected HtTA cells. Lane 3 and lane 4 show protein from uninfected and adenovirus infected puromycin resistant HtTA-rep1 cells derived from clone B1, respectively.

Figure 21:
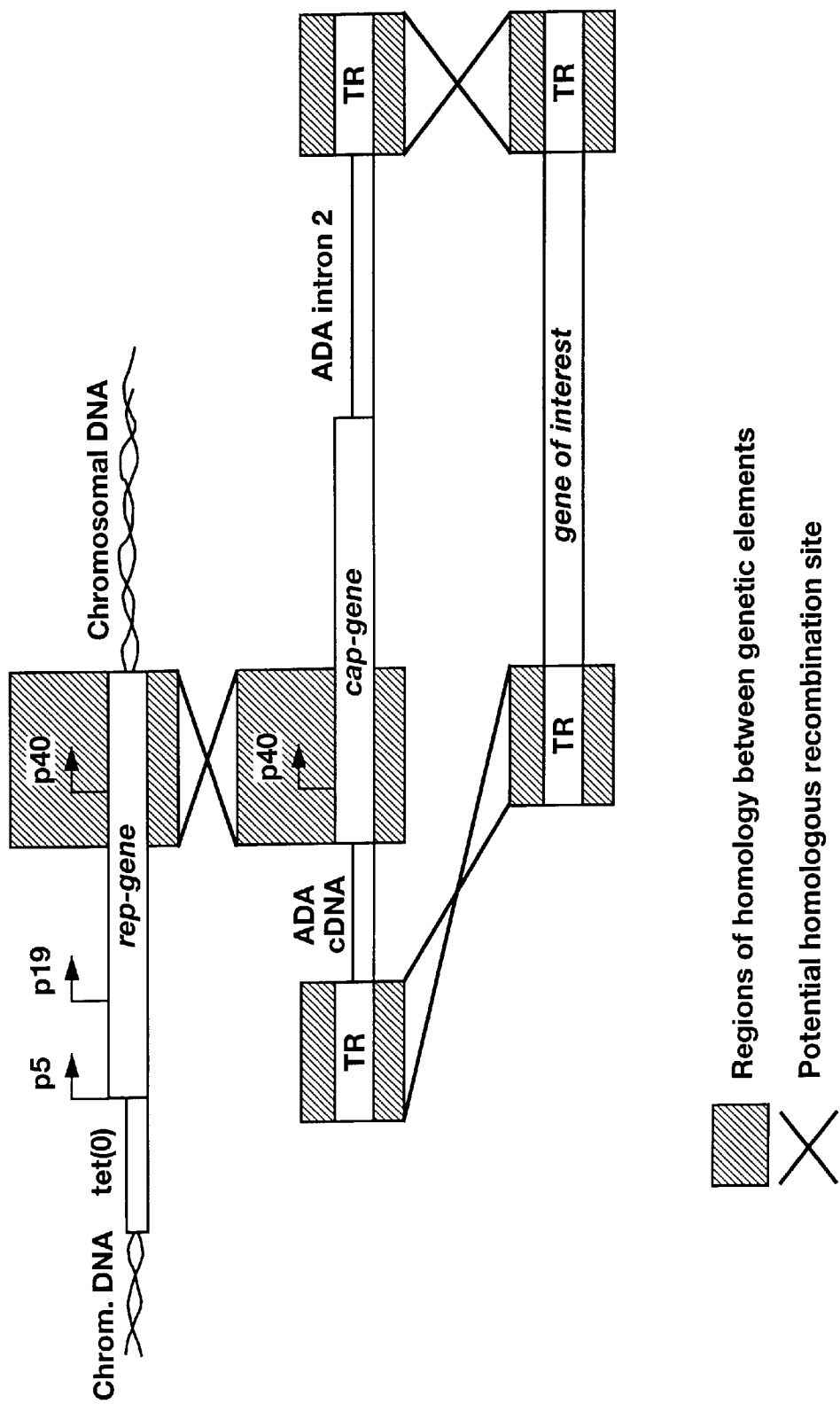

FIG. 21 shows regions of homology in the genetic elements important for the production of rAAV in the rAAV-packaging cell line of the present invention. Depicted are a rep-expression cassette, an excisable and replicateable cap-expression cassette and a rAAV molecule. The region of homology or overlap between the different constructs is highlighted with grey boxes. Possible homologous recombination sites are indicated with a cross (x). TR=AAV inverted terminal repeat. ADA cDNA is part of the human Adenosine Deaminase cDNA. ADA intron 2 is part of human Adenosine Deaminase intron 2.Chrom. DNA is a schematic representation of chromosomal DNA flanking the rep-expression cassette. Tet(o) indicates the tet$^R$-VP16 binding region in the promoter driving rep-expression. P5, p19 and p40 depict the position of the endogenous AAV-promoters p5, p19 and p40.

DETAILED EXPLANATION OF THE INVENTION ON THE BASIS OF AAV

The present invention is based on our finding that cap-gene expression is absent or just barely detectable when a cap-gene, physically linked to a variety of promoters, is introduced stably, into cells. Similar results were obtained using cap-constructs in which a cap-gene was placed under transcriptional control of its native promoter or of an inducible promoter to avoid possible toxicity. These results were striking, since the same promoters directed moderate to very high amounts of cap-gene expression when introduced transiently into cells. In the latter case, most of the introduced DNA is present in an episomal form and not integrated into the host cell genome, whereas stably transduced cells carry integrated constructs. Moreover, compared to the number of copies of the transgene in stably transfected cells, the number of copies of the transgene in transiently transfected cells is much higher. According to the present invention, cap-expression is dependent on the presence of the capsid DNA in an episomal form in the nucleus of cells, preferably in high copy numbers. This also explains earlier observations that in a lytic infection of AAV, first the rep-gene is expressed, and only later in the infection, when sufficient molecules have accumulated in the nucleus of the cells, the cap gene is expressed in significant quantities. The switch from an early gene expression pattern to a late gene expression pattern for AAV is determined by the number of cap-gene copies that have accumulated due to the early gene expression of AAV. A regulating mechanism based on the number of accumulated gene copies is a striking adaptation in an evolutionary perspective. AAV is a dependovirus and, as such, relies for its replication on a co-infecting helper virus. However, it also competes with the co-infecting virus for host cell derived proteins and basal components, such as nucleotides and energy-carriers. One way to be successful under this pressure is to ensure maximal replication in the early phase of the replication cycle. It is not desirable to efficiently package genomes and thereby to extract templates from the replication pool early in the replication cycle, since it significantly slows down the otherwise exponential increase in the number of templates. When the number of gene copies is low, efficient packaging function is not desired since it removes AAV templates from the replication pool, which interferes with the accumulation of maximal amounts of AAV-DNA in the shortest possible time. For autonomous viruses, early (replicative) and late (packaging) gene expression patterns are also favored to circumvent and out-compete the immune apparatus. However, for such viruses a strong dependency on copy numbers is probably not so crucial as in a co-infection setting.

The underlying trigger by which an increase in the number of copies is detected and stimulates the accumulation of cap-RNA is not known. One possibility is that negative acting proteins, such as repressors, bind to the AAV-cap DNA and prevent transcription. An increase in the number of templates also increases the number of binding sites for the repressor. When replication continues, a point is reached where there is not sufficient unbound repressor left in the nucleus of the infected cell to inhibit all new templates formed. When replication continues beyond this point, templates are no longer bound by the repressor and transcription can proceed.

In the present invention, a conditionally replicating system triggers the expression of an otherwise difficult to express gene, such as the AAV-cap-gene. One system relies on the AAV-replication machinery. However, to avoid use of AAV-ITR sequences for the rescue, replication and accumulation of the cap-gene, alternative replication systems can be used. The perhaps most well known replication system in the art is the replication system based on the Polyoma virus simian virus 40 (SV40). The Polyoma viruses (Polyomavirinae) are a subfamily of the Papovaviridae, a family of small, non-enveloped viruses with icosahedral capsids. Members of this family are, among others, the rabbit papilloma virus, mouse polyoma virus and simian virus 40 (SV40). Their genomes are single molecules of covalently closed, superhelical, double stranded DNA that replicate in the nucleus (reviewed in$^{32}$) These small viruses, particularly SV40, have been intensively studied. Their genomes can be divided into early and late regions. In addition to this, each Polyoma virus genome contains a single unique origin of DNA replication. The early region is transcribed and expressed early in the replicative cycle and continues to be expressed at late times after infection. In case of SV40, the early region encodes the small and large T-antigen. The large T-antigen is the only viral protein required for viral DNA replication. Large T-antigen will also replicate heterologous DNA molecules containing an SV40 origin of replication. This property of SV40 large T-antigen was exploited in COS-cells. The COS-1 and COS-7 monkey kidney cell lines express wild-type SV40 large T-antigen and contain integrated SV40 DNA carrying a deletion of sequences within the origin of replication of SV40$^{33}$. When SV40 origin of replication containing molecules are introduced into COS cells, the COS cells will replicate these heterologous molecules.

The present invention uses the SV40 replication system for the intracellular amplification of cap-DNA. The subsequent enhanced cap-expression can thus be used to package rAAV.

AAV-ITR sequences useful in the invention are obtained from AAV serotypes 1, 2, 3, 4 or 5. Alternatively, mutant or recombinant ITR sequences can be used, which retain the essential properties of the AAV-ITR prototype, which are described in Lefebyre et al$^{34}$.

For most applications of the invention, the helper virus functions are required for efficient packaging of recombinant AAV. In these cases, the helper virus is inactivated or separated physically from the recombinant AAV virions before using the recombinant AAV virions for the transduction of cells. The present invention, however, also provides a method to package recombinant AAV vectors by adding the recombinant AAV DNA to protein extracts or mixtures of protein extracts of cells that expressed all or part of the relevant proteins for the replication and packaging of recombinant AAV. When protein extracts are used from cells expressing only some of the relevant proteins for packaging of recombinant AAV, the missing proteins can be supplied externally in purified form. Thus, the present invention obviates the need for using helper virus in the production process.

The rep-gene can be derived from anyone of AAV serotypes 1–5, or functional analogs or parts thereof, including but not restricted to those obtained through the introduction of non-essential mutations in the rep-genes or through the isolation of genes with similar capabilities, such as the Human Herpesvirus 6 AAV-2 rep gene homologue[35].

The cap-gene can be derived from any one of the AAV serotypes 1–5 or functional analogs or parts thereof, obtained, but not restricted to, through non-essential mutations in the cap-genes. In addition, the cap-gene sequences can be altered through the replacement or addition of sequences rendering the produced virion with new or altered target cell specificity or with improved features for the purification and concentration of rAAV particles, such as a peptide tag.

Recombinant AAV virions produced according to the invention are purified and concentrated using biological, physical or chemical separation techniques known in the art including, but not limited to, antibody affinity purification, density gradient centrifugation or ion exchange chromatography. Alternatively, said virions can be used in a crude unpurified form.

As used herein, the term "functional analog or part" refers to a derivative with the same activity in kind, though not necessarily in the same amount, as the original.

It is to be understood that only certain embodiments of the invention are illustrated by examples and that the examples should not be considered restrictive in character. All modifications within the scope of the invention that may be contemplated by persons skilled in the art are considered to be part of the present invention.

The invention is illustrated by the following non-limiting examples wherein the following materials and methods were employed. The entire disclosures of each of the literature references cited hereinafter are incorporated by reference herein.

One of the embodiments of the invention illustrated by the example is the generation of a rep and cap complementing packaging cell line for the production of rAAV. Examples 1 and 2 describe the generation of a stable cell line expressing the rep-gene. Examples 3 and 4 describe the generation of a cell line expressing the cap-gene. For both genes, a solution to the expression problem was found in inducible expression systems developed for this purpose. For the rep-gene products, an improved tetracycline regulated expression system was developed. For the cap-gene products, the invention teaches that high level expression is only obtainable upon replication and accumulation of the cap-DNA. A conditionally replicating system was developed in which cap-expression can be induced. An added advantage of the conditionally replicating system is that expression of cap can be regulated such that expression occurs late in the replication cycle of AAV, thus mimicking the wild type AAV expression pattern in a lytic infection. Example 5 describes an alternative method to obtain a conditionally replicating system for the expression of cap-gene products. Example 6 describes methods for the generation of a rep-and cap-complementing cell line useful for the generation of recombinant AAV.

EXAMPLES

Example 1
Transient Expression of Rep and Cap From Tetracycline Repressor Operator Regulated Constructs The classical inducible eukaryotic promoters like, for instance, heat shock promoters, the mouse methallothionine promoter or the mouse mammary-tumor virus long terminal repeat promoter, respond to heat shock, heavy metals or hormones[36-43]. These promoters are, in principle, not ideally suited to inducibly express (toxic) genes, since the promoters are not completely silent in the uninduced state[39] and/or because the inducing principle induces pleiotropic effects in the target cells[44]. A new generation of regulated promoters has adapted parts from bacterial transcription units for use in eukaryotic cells[45-52]. These artificial transcription units are adapted from the lac repressor-operator-inducer system or the TN10-specific tetracycline resistance operon from E. coli. Three different systems have been described: i) the prevention of transcription initiation by well placed repressor-operator complexes on the promoter[45-47, 51]; or ii) by blocking the RNA-polymerase II during elongation by a repressor-operator complex[48, 51]; or iii) the activation of a minimal TATA-box replenished with operator sequences which can be recognized by an artificial transactivator (tA). The tA consists of the operator binding component derived from the lac-repressor or the tetracycline repressor and the transcription activating domain from VP16, a Herpes Simplex Virus encoded transcription activator[49, 50, 52].

Specifically, the latter system, where a minimal promoter is combined with operator sequences from the tet-repressor, is suitable for the regulated expression of foreign genes in eukaryotic cells. Since the tet-repressor operator sequences have no functional homologue in eukaryotic cells, these promoters are practically inactive in the presence of low concentrations of tetracycline or related compounds such as doxycycline[52, 53]. Stable cell lines exist that constitutively express the tetracycline-repressor VP16 fusion gene (tA). We have used a HeLa cell line HtTA expressing the tA constitutively[52] to test the possibility of obtaining tetracycline regulated expression of rep.

Figure 1:
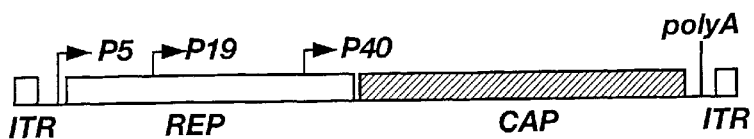
FIG. 1 depicts the structure and the genome organization of wtAAV.
Figure 1:
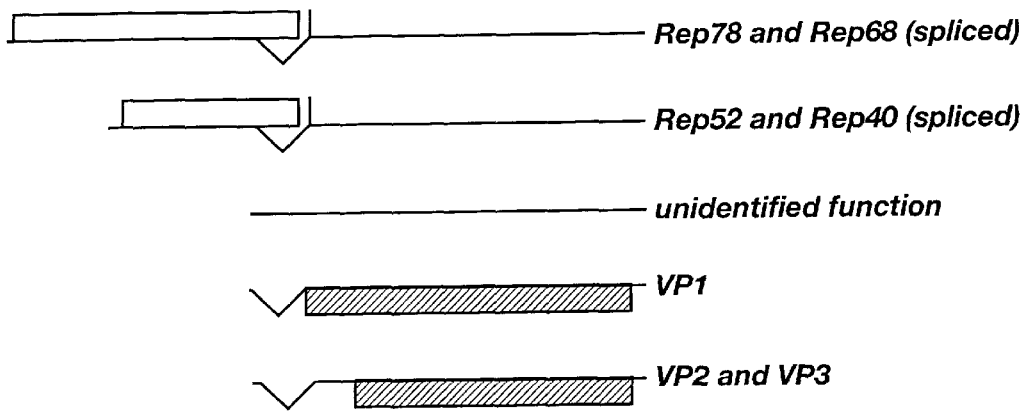
Figure 2:
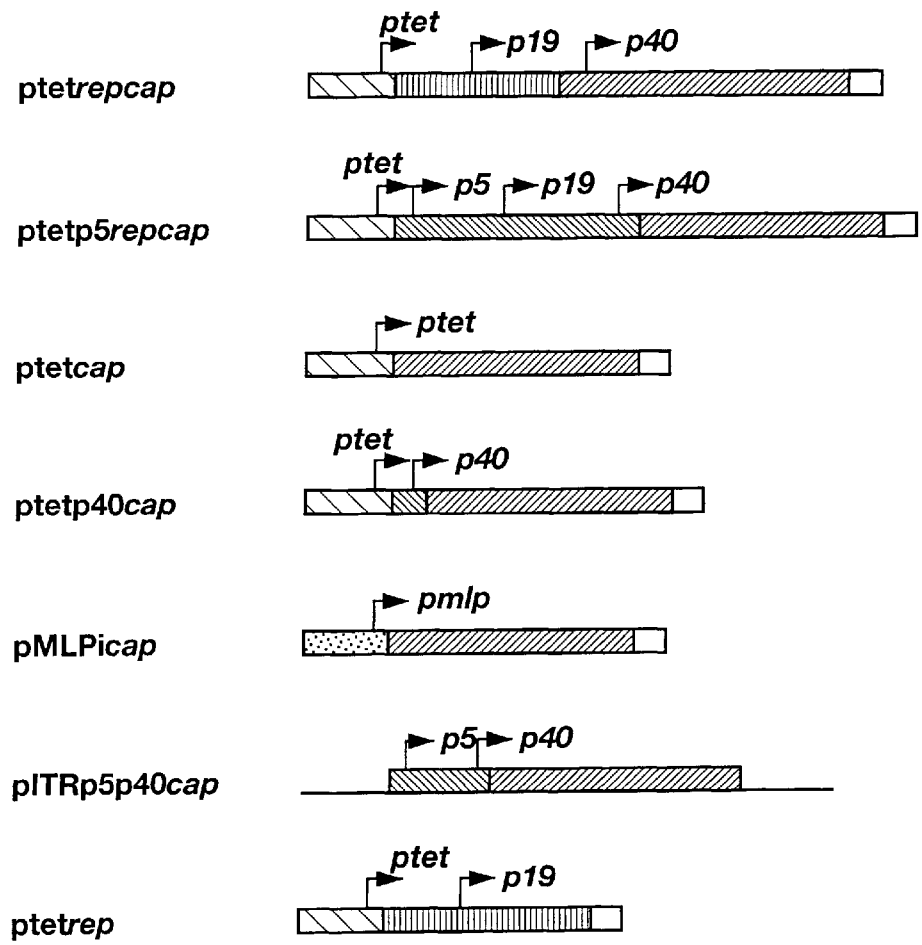
FIG. 2 is a schematic representation of the constructs
Figure 3:
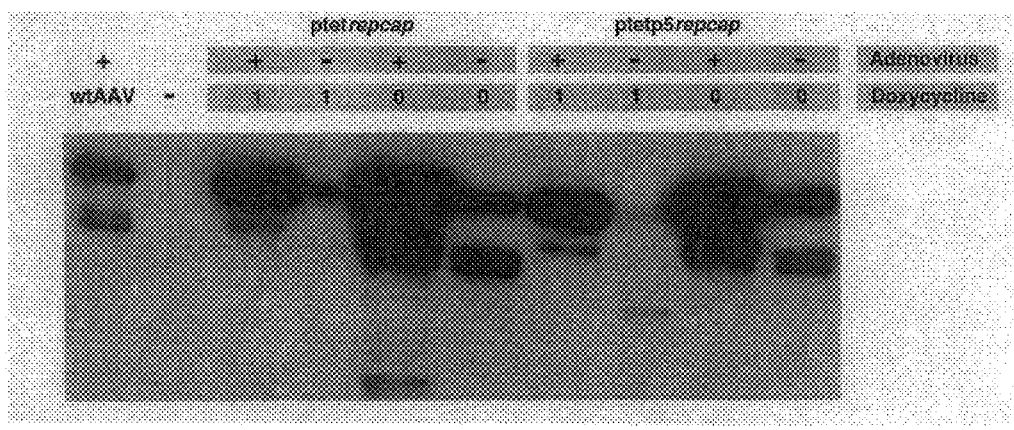
FIG. 3 depicts regulated expression of Rep78 and Rep68 from ptetrepcap and ptetp5repcap in HtTA cells two days after transfection of the construct. Protein extracts from transfected cells were analyzed by immunoblotting with an anti-Rep antibody 7B7.32, a kind gift from Dr. N. Muzyczka. When indicated (+), the cells had also been infected with adenovirus (multiplicity of infection (moi) 20) at the time of transfection. When indicated (1), the cells were transfected and cultured in the presence of 1 ug/ml doxycycline. Protein extract from adenovirus (moi 20) and wtAAV (moi 2) infected HtTA cells (wtAAV) served as controls for the production of Rep78 and Rep68. Protein from HtTA cells served as a negative control (lane marked with (–))

For this purpose, we generated constructs containing the rep and cap coding regions, in which large Rep protein expression was placed under control of the tet-operon (FIG. 2). In the construct ptetrepcap, we exchanged the p5-promoter with the tet(o) promoter, whereas in the construct, ptetp5repcap, we cloned the tet(o) in front of the p5 promoter. It has previously been shown that the adeno-associated virus P5 promoter contains two motifs centered at −60 and +1 relative to its transcription initiation site that mediate transactivation by the 13S E1A protein. A cellular factor, YY1, that binds to the motif was identified, and its cDNA was cloned. YY1 is a 414-amino-acid zinc finger protein that represses transcription when bound upstream of heterologous basal promoters; E1A-proteins relieve the repression and activate transcription through YY1[54]. With the ptetp5repcap construct we intended to study whether additional silencing of the tet-operon was beneficial for the generation of inducible rep-expressing cells. To determine the activities of the promoters, the constructs were transfected into HtTA-cells in the presence or absence of doxycycline and in the absence or presence of adenovirus. Protein was extracted after two days and Western blotted. The filters were incubated with the Rep78, Rep68 specific monoclonal antibody 7B7.32 (a kind gift of Dr. R. J. Samulski). Both ptetrepcap and ptetp5repcap expressed Rep78 and Rep68 in a doxycycline regulated fashion in HtTA cells and, for both constructs, the expression was upregulated upon adenovirus infection (FIG. 3). Expression of Rep78 and Rep68 in the uninduced state (i.e. with doxycycline and without adenovirus) is markedly reduced with the ptetp5repcap, as compared to ptetrepcap under the same conditions. These results prove that i) it is possible to obtain regulated expression of Rep78/Rep68 using the artificial tet-operon and ii) adenovirus infection up-regulates expression of the rep-gene in both constructs. In the tetp5repcap construct, the adenovirus effect could be mediated by adenovirus responsive elements in the p5 promoter, such as the two YY1-sites. In the tetrepcap construct, however, the expression enhancing effect of adenovirus infection must be mediated by an alternate mechanism, possibly by a direct effect on the tet(o) and the minimal TATA-Box or an adenovirus responsive element in the AAV-genome or by post transcriptional mechanisms. We observed that the basal rep-expression of the ptetp5repcap construct is reduced compared to ptetrepcap. The difference between the constructs is a small AAV-fragment containing part of the p5-promoter and the 5' untranslated region mRNA encoding the large Rep-proteins. Identified cis-acting sequences in the extra fragment that alone or in combination could mediate the reduced basal level expression are a major late transcription factor (MTLF) site, the two YY1-sites[54] and the Rep-binding site[55] in the P5 promoter.

Figure 4:
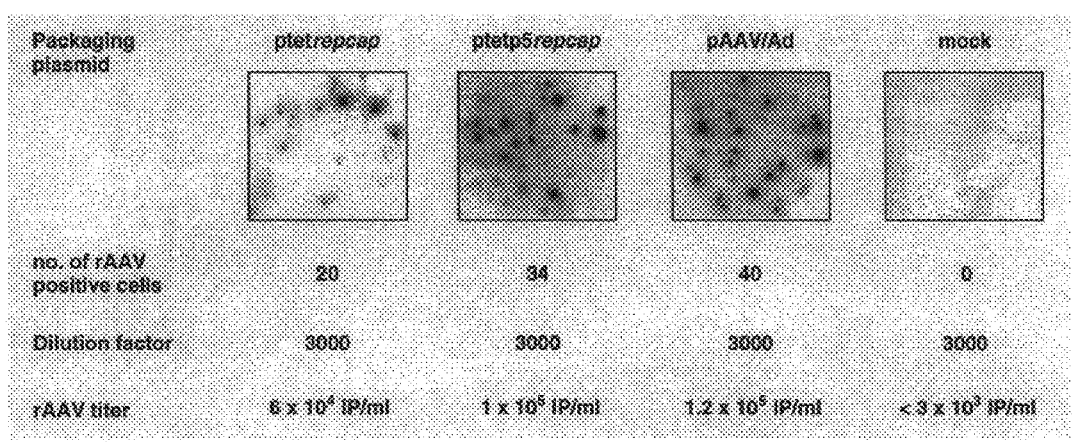
FIG. 4 depicts a replication center assay specific for recombinant AAV IG-CFT, a recombinant AAV vector containing the human b-globin gene and the neo-gene[31]. Recombinant AAV was isolated from adenovirus infected (moi 20) HtTA cells transfected with recombinant AAV construct pIG-CFT together with either ptetrepcap and ptetp5repcap as packaging constructs. The packaging plasmid pAAV/Ad served as a positive control for the assay and Adenovirus-infected HtTA cells served as a negative control for the assay.

To verify whether the rep-gene expression was functional, the constructs were used to produce recombinant AAV. The constructs were co-transfected with a plasmid pIG-CFT, carrying a recombinant AAV vector[31], into adenovirus infected HtTA cells. After three days, recombinant AAV was isolated and titrated in a replication center assay (RCA) by serial dilution of the recombinant AAV stock on adenovirus and wtAAV infected 293 cells[56] as described in Einerhand et al[31]. The ptetrepcap packaging construct produced recombinant IG-CFT with a titer of $20 \times 3 \times 1000 = 6 \times 10^4$ Infectious Particles (IP) per ml, whereas the ptetp5repcap packaging *construct produced recombinant IG-CFT with a titer of $6 \times 3 \times 1000 = 1.8 \times 10^4$ IP per ml (FIG. 4). Thus the AAV-protein coding domain is functional in both constructs Example 2
Stable Cell Lines Expressing High Regulated Levels of Rep78 and Rep68

Figure 5:
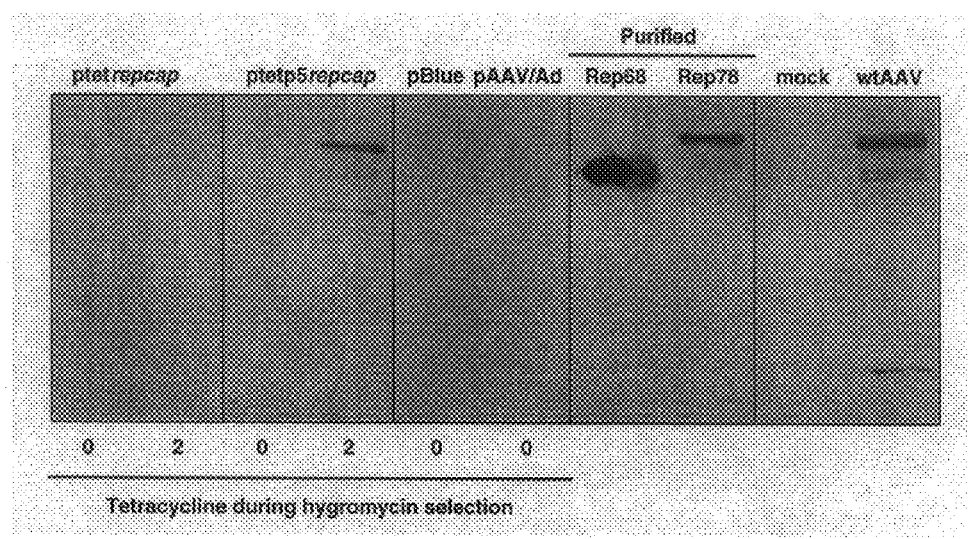
FIG. 5 depicts a regulated expression of Rep78 and Rep68 from ptetrepcap and ptetp5repcap in stably transfected HtTA cells. HtTA cells were co-transfected with the indicated constructs and pX343, a hygromycin B resistance gene containing plasmid. The cells were selected for hygromycin B resistance for 14 days starting two days after transfection. During transfection and selection, the cells were grown in the absence (o) or presence (2) of 2 ug/ml tetracycline. Following selection, the cells were seeded in medium devoid of tetracycline and infected with adenovirus (moi 20). Protein was extracted after 48 hours and immunoblotted using an anti-Rep specific antibody 7B7.32. The lanes marked mock were from left to right, transfected only with the hygromycin construct and untransfected HtTA cells. The lane marked wtAAV contains protein from HtTA cells infected with adenovirus (moi 20) and wtAAV (moi 2). The lanes marked Rep68 and Rep78 contain purified Rep68 and Rep78 respectively, a kind gift from Dr. S. Zolotukhin.

We next generated stable cell lines expressing in a regulated fashion high levels of Rep78 and Rep68. HtTA cells were transfected with ptetrepcap or ptetp5repcap together with plasmid pX343 containing a hygromycin B resistance gene under transcriptional control of the SV40 promoter in a ratio of 10:1 (w/w), respectively. Transfections were performed in the presence or absence of 2 ug/ml tetracycline. Two days after transfection, the medium was replaced by medium containing 400 ug/ml Hygromycine B with or without 2 ug/ml tetracycline. This medium was refreshed every 3 to 4 days. After two weeks, the colonies in the dishes were trypsinised, seeded in medium without tetracycline and infected with adenovirus. After two days, the cells were collected and total protein was Western blotted. Rep-protein expression was analyzed using the Rep78/Rep68 specific monoclonal antibody 7B7.32 (FIG. 5). In untreated cells (lane HtTA) and in pBluescript transfected HtTA cells (pBlue), no Rep-specific bands are detected. In the positive control lane, HtTA infected with wtAAV-2, Rep78 and Rep6B are easily detected. Rep68 runs as a double band in SDS-page (M.E. unpublished results). Purified Rep78 and Rep68 protein (kindly provided by Dr. Nick Muzyczka) are in the lanes marked as Rep78; Rep68 served as size markers for the respective proteins. When pAAV/Ad[7] was transfected or when the ptetrepcap construct was transfected, no Rep78 or Rep68 could be detected in the adenovirus infected pools irrespective of whether the pools were generated in the absence or presence of tetracycline (FIG. 5). This complies with the notion that even low levels of Rep78 and Rep68 are not tolerated by the cells. The ptetp5repcap construct, in contrast, does express significant amounts of Rep78 and Rep68 in a regulated fashion (FIG. 5). Pools generated in the presence of tetracycline, when the tet(o) is inactive, express Rep78 and Rep68 upon removal of the tetracycline from the medium. However, when pools were generated in the absence of tetracycline, when the tet(o) is active, no expression of Rep78 and Rep68 could be detected. These results indicate the presence of sequences in the p5 promoter that down-regulate expression of Rep78 and Rep68. The sequences in the AAV p5-promoter responsible for this phenomenon could be the binding sites for adenovirus major late transcription factor (MTLF), Rep78 and Rep68 or YY1[54].

Example 3
Low Cap-Gene Expression in Stable Transfected Cell Lines

We analyzed the expression of the cap-gene in the stable transfected pools described above. No expression of VP1, VP2 or VP3 could be detected (not shown). The presence or absence of tetracycline and/or adenovirus had no effect on expression of cap. Assuming that the p40 promoter was not functional in the context of the constructs we had generated, we designed three new constructs. In these constructs, different promoters, including inducible promoters, were cloned in front of the cap-gene. The constructs ptetcap, ptetp4ocap, pMLPicap (FIG. 2) were transfected in HtTA cells in the presence or absence of adenovirus and, for the tet(o) containing constructs, also in the absence and presence of doxycycline. After two days, the cells were harvested and protein was analyzed on Western blot for cap-protein expression. All constructs were able to express cap, albeit not under all conditions tested (not shown). Adenovirus infection had a general enhancing effect on expression of cap and for the tet(o)—containing constructs, expression of cap increased upon induction of tet(o) (not shown). We next generated stable cap cell lines by transfecting the cap-constructs in HtTA cells. For tet(o) containing constructs transfections were performed both in the presence and in the absence of tetracycline. Expression of the cap-gene was analyzed two days after the cells were seeded in medium without tetracycline and were infected with Ad. Cap-encoded protein could not be detected in these cell lines (not shown). We concluded that the various promoters were not capable of directing cap-expression in stable transfected cells, an unexpected result since the same promoters were capable of directing cap-expression when transiently transfected.

Example 4
High Level Cap-Gene Expression in Stable Transfected Cells

The finding that stable transfectants did not express significant amounts of cap-protein was unexpected. Several reasons can be put forward to explain this result. For instance i) cap-expression is toxic to cells. It is not very likely that cap-expression is toxic to the cells since there was no difference in the number of colonies with control transfections and we observed no increase in the number of hygromycin B resistant colonies with inducible cap-constructs (not shown).
ii) cap-gene expression is inhibited once the cap-gene is integrated into the host cell genome.
iii) cap-DNA needs to be present in the cell in many copies to titrate out a putative cap-DNA binding factor that inhibits expression from a proximal promoter.
iv) cap is low for any of the promoters tested, whether the construct is integrated in the host cell genome or not. Expression would then become detectable when sufficient templates for transcription are present in the cells, as in a transient CaPO4 transfection.

To test whether one or more of these hypotheses were valid, we generated a construct that, when integrated in the host cell genome, could be induced to excise and replicate. For this purpose, we generated the construct pITRp5p40cap, in which the cap-gene is flanked by two AAV-ITR. In cells stably transfected with this construct, the cap-gene can be excised from the genome and replicated by supplying the Rep-proteins in trans. The replicated cap-gene copies accumulate extrachromosomaly, thus mimicking the extrachromosomal state of the DNA in a transient transfection. One of the differences with a transfection of a plasmid is the linear state of the replicated DNA. We chose a replicating system for the reason that in a productive wild-type AAV infection, the template for cap-expression is also replicated.

Figure 6:
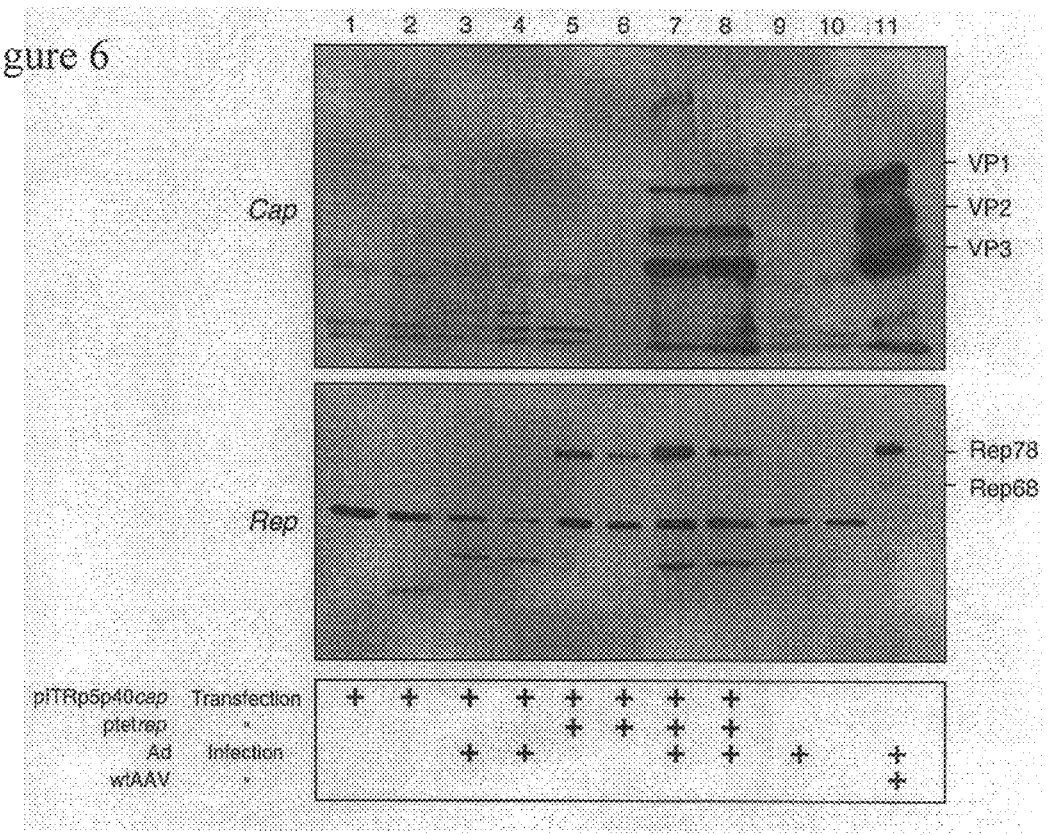
FIG. 6 depicts an expression of pITRp5p40cap in HtTA cells two days after transfection. The panel marked Cap, is an immunoblot with an anti-Cap specific antibody B1, a kind gift from Dr. J. Kleinschmidt. Indicated are the locations of the proteins VP1, VP2 and VP3. The panel marked Rep, is an immunoblot with an anti-Rep specific antibody 7B7.32, a kind gift from Dr. N. Muzyczka. Indicated are the proteins Rep78 and Rep68. In the table below is depicted (+) when the cells were transfected with pITRp5p40cap and/or ptetrep and/or were infected with adenovirus (moi 20) or wtAAV (moi 2) at the time of transfection.

We first tested the transient expression capabilities of the construct in HtTA cells (FIG. 6). No expression was detectable when the construct was transfected alone or together with ptetrep. When the construct was transfected into adenovirus infected HtTA cells VP3, protein was expressed (FIG. 6, lanes 3, 4). However, when the construct was transfected into adenovirus infected HtTA cells together with ptetrep, all three capsid proteins were readily detectable.

Figure 7:
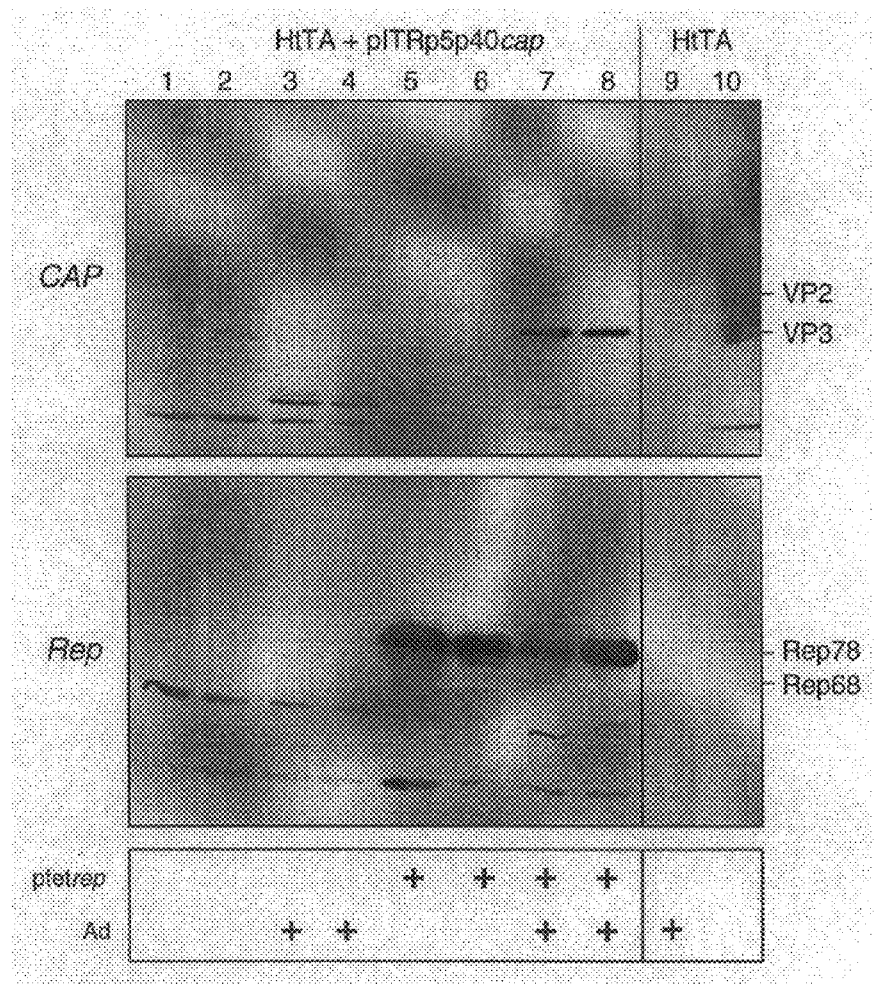
FIG. 7 depicts an expression of VP1, VP2 and VP3 in HtTA cells stable transfected with pITRp5p40cap (lane 1–8). The cell lines HtTA-cap1 (lanes 1,3,5,7) and HtTA-cap2 (lanes 2,4,6,8) were analyzed for cap-expression. Protein was isolated from untreated HtTA-cap cells (lane 1 and 2); from cells infected with adenovirus 48 hours before protein isolation (lanes 3 and 4); from cells transfected with ptetrep 48 hours before protein isolation (lanes 5 and 6) and from cells infected with adenovirus (moi 20) and transfected with ptetrep 48 hours before protein isolation (lanes 7 and 8). Adenovirus (moi 20) infected HtTA cells served as a negative control. The panel marked Cap, is an immunoblot with an anti-Cap specific antibody B1, a kind gift from Dr. J. Kleinschmidt. Indicated are the location of the proteins VP2 and VP3. The panel marked Rep, is an immunoblot with an anti-Rep specific antibody 7B7.32, a kind gift from Dr. N. Muzyczka. Indicated are the proteins Rep78 and Rep68.
Figure 8:
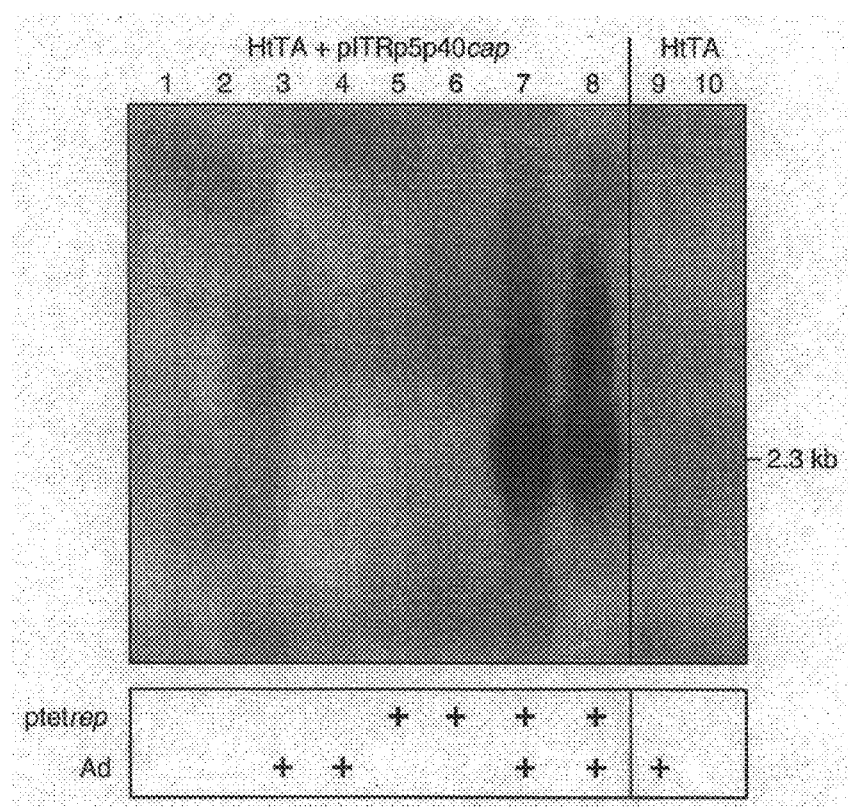
FIG. 8 depicts an expression of cap-specific RNA in HtTA cells stable transfected with pITRp5p40cap (lane 1–8). Treatment of the cells and lane numbering is the same as in FIG. 7. Lane 10 contains RNA from untreated HtTA cells. Instead of protein, total RNA was isolated and Northern blotted. The filters were hybridized with a cap-specific probe that contained no sequence overlap with ptetrep. Indicated is the 2.3 kb RNA that hybridized to the probe.
Figure 9:
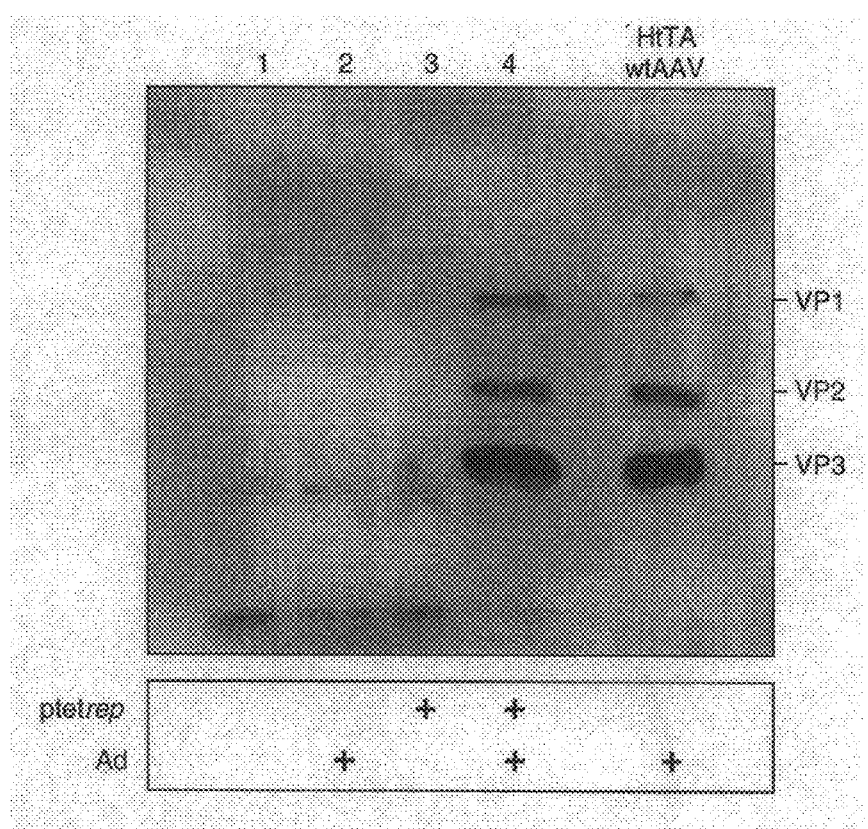
FIG. 9. is an expression of VP1, VP2 and VP3 in HtTA-cap2 cells (lane 1–4). Shown is an immunoblot with an anti-Cap specific antibody B1 of protein isolated from untreated cells (lane 1), from cells that had been infected with adenovirus (moi 20) two days before protein isolation (lane 2), from cells transfected with ptetrep two days before protein isolation (lane 3) and from cells infected with adenovirus (moi 20) and transfected with ptetrep two days before protein isolation (lane 4). The lane marked HtTA wtAAV contains protein from HtTA cells infected with adenovirus (moi 20) and wtAAV (moi 2) two days before protein isolated. VP1, VP2 and VP3 are indicated.

Next, we examined the stable expression capabilities of the pITRp5p40cap construct. The construct was transfected into HtTA cells together with the plasmid pX343 carrying the hygromycin resistance gene in a ratio of (10 to 1). The cells were selected after 14 days for hygromycin B resistance and two independent polyclonal cell lines, designated HtTA-cap1 and HtTA-cap2, were generated. No expression of cap-proteins could be detected (FIG. 7, lanes 1–2). Expression of adenovirus proteins or rep-proteins did not transactivate the p40-promoter (FIG. 7, lanes 3–4 and 5–6 respectively). The latter observation is in accordance with previous art in which transactivation of the p40-promoter by the large Rep-proteins was found in some cases and not in others[21, 57]. However, when HtTA-cap1 and HtTA-cap2 cells were both infected with adenovirus and transfected with ptetrep two days before harvest, VP3 protein was readily detectable. VP1 and VP2 were also detected but the signal was not high (FIG. 7, lane 7–8). Translational mechanisms for the presence or absence of cap-proteins could be excluded since protein expression correlated with the presence of cap-specific RNA (FIG. 8). To verify that all three capsid proteins could be produced, we repeated the experiment on HtTA-cap2 cells. This experiment confirmed the previous experiment but now VP1, VP2 and VP3 are clearly distinguished (FIG. 9). The relative abundance of the three proteins resembles that of a wild-type AAV infection. This is important to warrant the production of functional particles. For instance, similar to the result mentioned above, Dr. J A Kleinschmidt observed in stable cell lines a low expression of cap protein. However, in addition to the low level of expression, VP2, which is crucial for capsid formation[58], was consistently not detectable (personal communication).

Figure 10:
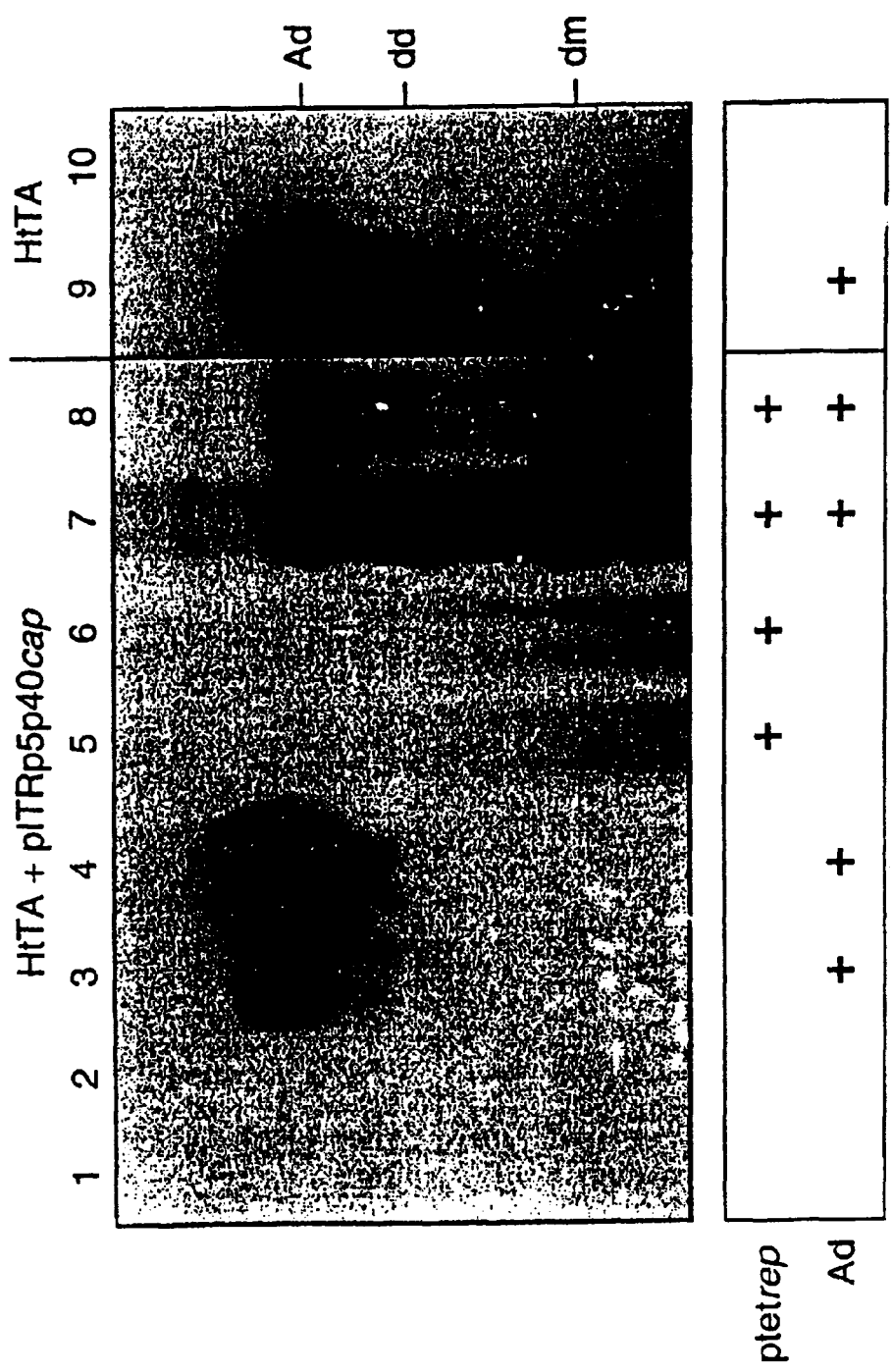
FIG. 10 depicts a Hirt-extract DNA from HtTA-cap1 cells and HtTA-cap2 cells. Treatment of the cells and lane numbering is the same as in FIG. 7. Lane 10 contains Hirt-extract from untreated HtTA cells. Episomal DNA was isolated and analyzed on a Southern blot. The filters were hybridized with a cap-specific probe that contained no sequence overlap with ptetrep. Indicated are the duplex monomer (dm), the duplex dimer (dd) and an adenovirus cross hybridizing band (Ad).

To test the presumption that cap-DNA was excised from the genome and replicated, Hirt-extract DNA was analyzed. Expression of cap-protein correlated with the detection of recombinant AAV replication intermediates in the cells (FIG. 10). Thus, one or more steps involving rescue from the genome, and subsequent replication and accumulation of the capsid gene, were required before cap-expression could be detected.

Figure 11:
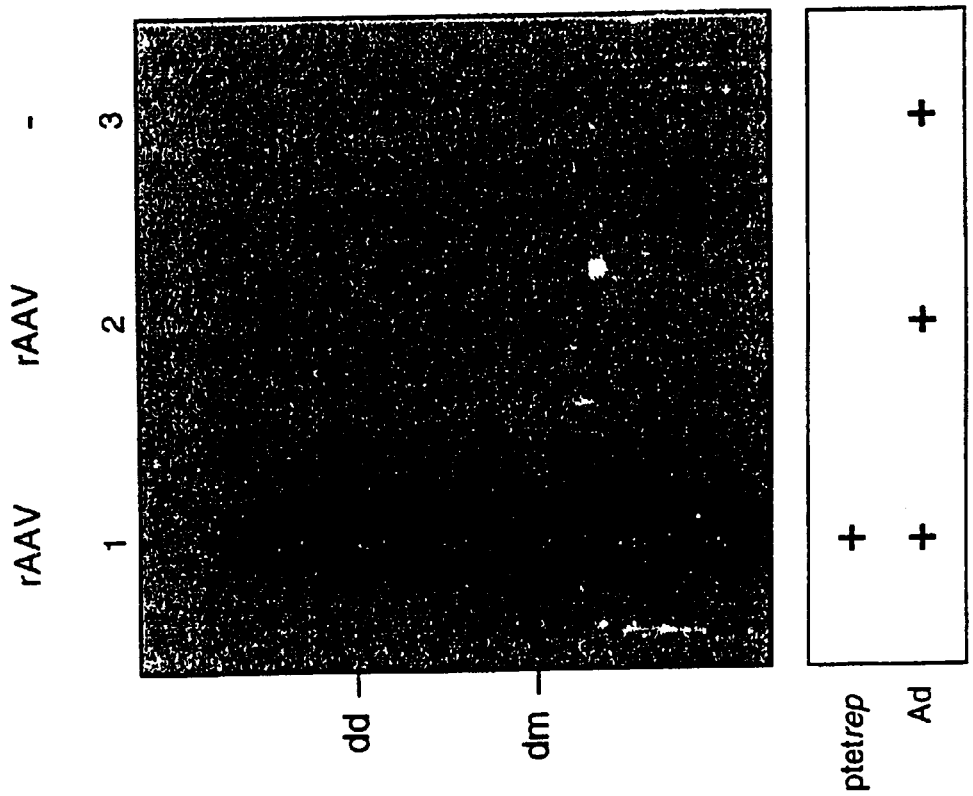
FIG. 11 depicts a Hirt-extract from HtTA cells infected with rAAV produced by HtTA-cap2 cells. Shown is a Southern blot hybridized with a cap-specific probe that contains no sequence overlap with ptetrep. One day before Hirt-extraction, the HtTA cells were infected with rAAV and adenovirus (lane 1, 2) and transfected with ptetrep (lane 1). As a negative control, a mock rAAV-isolate from HtTA-cap2 cells infected with only adenovirus (moi 20) was used to infect HtTA cells also infected with adenovirus (lane 3).
Figure 12:
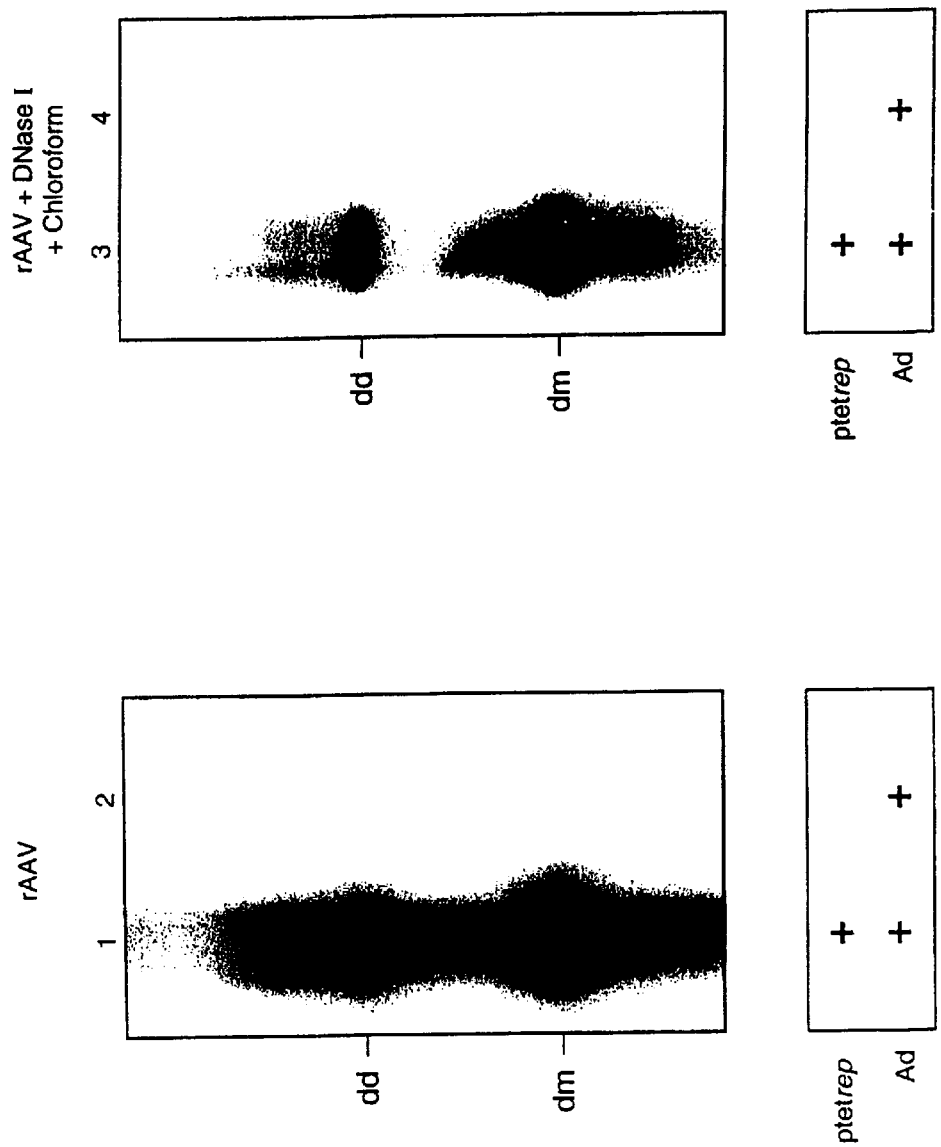
FIG. 12 depicts a Southern blot of Hirt-extract from adenovirus HtTA cells infected with rAAV produced by HtTA-cap2 cells. The Southern blot was hybridized with a cap-specific probe that contains no sequence overlap with ptetrep. One day before Hirt-extraction, the adenovirus infected HtTA cells were transfected with ptetrep (lane 1 and 3) and either infected with rAAV (lane 1 and 2) or infected with rAAV that had been pretreated with DNase I (1 mg/ml) for 30 min. at 37° C. and chloroform (lane 3 and 4).

To verify whether the detected cap-expression led to the production of functional and intact capsids, HtTA-cap2 cells were infected with adenovirus and transfected with ptetrep. After 48 hours, a crude rAAV was prepared. The crude rAAV preparation was used to infect normal HtTA cells infected with adenovirus and transfected with ptetrep. After 24 hours, Hirt-extract DNA was Southern blotted and hybridized with a cap-specific probe. Replication of the cap-containing rAAV was readily detectable (FIG. 11, lane 1). When a control rAAV-preparation was isolated from HtTA-cap2 cells infected with adenovirus in the absence of a rep-construct (i.e. when cap-expression was not detected), no replication could be detected upon infection of permissive HtTA cells (i.e. no transmissible rAAV had been produced). DNaseI digestion and chloroform treatment reduced the concentration of transmissible rAAV approximately two-fold FIG. 12, indicating the formation of intact AAV-particles by the HtTA-cap2 cell line.

Example 5

Stable Cell Lines Expressing Cap in a Regulated Fashion Using Large T-Antigen Based Replication Systems An SV40 replication system useful for the expression of cap may be prepared as follows. Two SV40 origins of replication are cloned as a direct repeat flanking the cap-gene, allowing a PCR like amplification of the cap-DNA in permissive cells. Expression of cap can be regulated by the SV40 early gene promoter, the endogenous p40 promoter or other strong constitutive promoters. The construct can be co-transfected into cells together with pX343 or other plasmids containing dominant selectable marker genes according to methods described above. Cell lines that can be used for the generation of the rAAV-packaging system should meet the following criteria: the cells should be able to sustain AAV-replication and SV40 replication; the cells should be compatible with the tetracycline regulated expression system described by Bujard et al (i.e. they should not exhibit a high basal level expression of the tet(o) minimal TATA-box element); the cells should not express E1A since it would activate the E1A responsive element in the p5-promoter fragment used in the improved tet(o) described in example 1; the cells should be permissive for YY1 mediated silencing of the p5-promoter; and, finally, the cells should, preferably, not exhibit rep-mediated inhibition of SV40 replication, like, for instance, COS cells[59]. A non-limiting example of such a cell line is COS-1[59].

Upon co-transfection of the construct with pX343, hygromycin B resistant colonies can be generated by adding the appropriate concentration of hygromycin B to the medium of the transfected cells. Individual colonies can be expanded and analyzed for large T-antigen induced replication and expression of cap by analyzing protein and Hirt-extract DNA from the cells one or two days after a transfection of the cells with an expression construct of large T-antigen.

Example 6

Generation of a General Packaging Cell Line For rAAV-Vectors

A cell line based on tetracycline and adenovirus regulated expression of rep, and AAV-ITR based replication and expression of cap, can be generated using the following general protocol. Transfection can be performed of tetp5repcap or suitable derivative with deletions in cap, into HtTA-cap2, together with a plasmid containing the dominant selectable marker gene gpt or zeocin (Stratagene) under transcriptional control of an SV40 early promoter. Transfection and subsequent selection should be performed in the presence of tetracycline or suitable analogs thereof. Deletion of cap-sequences from the rep-gene expression construct is desired to minimize the regions of overlap between this construct and the cap-expression construct, since extensive overlap will increase the chance of homologous recombination and facilitates the formation of wtAAV. However, while deleting cap-sequences from the rep-construct, it is important to leave enough information as to warrant adequate splicing of the messenger to produce Rep68 and Rep40. Rep-constructs with only the rep-coding domains, such as ptetrep, do not splice efficiently enough to produce significant amounts of Rep68. Splicing information can be contained in cis-acting sequences 3' of the rep-coding region in the form of splicing enhancers or inefficient splicing of rep-RNA in ptetrep can be the consequence of an interruption of an, as yet, unidentified mRNA producing a novel AAV protein (Kleinschmidt, personal communication). Following the appropriate selection for expression of the selectable marker gene, different colonies can be analyzed for inducible expression of rep by removing the doxycycline from the medium and infecting the cells with adenovirus. Separate colonies can be screened for the production of cap-DNA containing rAAV particles as described above. These cell lines could be useful for the production of different rAAV by transfecting the DNA containing the rAAV into the cells. A stable cell line can be generated or the DNA can be introduced by transfections for each rAAV preparation. A disadvantage of the packaging cell line is that such rAAV preparations will also contain a significant amount of cap-DNA containing rAAV. This can be reduced by altering the pITRp5p40cap construct in such a way that packaging of the replicated DNA is not possible. For instance, by adding non-essential DNA between the two ITR sequences, the size of the replicated DNA exceeds the packaging limit of AAV.

A cell line based on tetracycline and adenovirus regulated rep-expression and SV40 large T-antigen based replication and expression of cap can be generated using the following general protocol. Transfection of CV1 cells or HeLa cells can be performed with a construct containing the cap-gene flanked by two SV40 origins of replication together with a plasmid containing a dominant selectable marker gene. Following selection, individual clones can be split into two fractions. one half of the cells can be transfected with an expression construct for large T-antigen and screened for large T-antigen dependent replication and expression of the cap-gene. The other half of the cell lines that do express the cap-gene upon transfection, can be used to stably transfect the ptetp5repcap construct, or suitable derivatives with deletions in cap, and a tetp5 regulated SV40 large T-antigen construct. Preferably, these constructs are transfected together but without a construct containing a dominant selectable marker gene. In co-transfections, constructs usually integrate together in the same chromosomal position; thus an enhancer in the promoter driving the dominant selectable marker gene can stimulate the co-transfected inducible promoters. Following transfection, the cells can be seeded single cell per well in separate wells of a 96 well dish. After two weeks, the colonies can be split in two, one half of a colony can be reseeded into fresh 96 well plates and one half of the cells can be used to screen by PCR for the presence of rep and large T-antigen DNA. Colonies containing both DNA sequences can be expanded and analyzed for the tetracycline and adenovirus regulated expression of Rep78, Rep68, Rep52, Rep40, large T-antigen and small T-antigen on Western blots. Cells correctly expressing these proteins can be identified upon infection with adenovirus and transfection with a construct pUHD15-1[52] containing an expression cassette of the artificial transactivator tet[R]-Vp16. Functional expression of rep, cap and large T-antigen can be verified by transfecting the cells with pUHD15-1, pIG-CFT and infecting the cells with adenovirus. After two or more days, rAAV produced can be analyzed with a replication center assay specific for pIG-CFT. Cell lines that produce rAAV in such a way can be turned into a general packaging line for rAAV by stably transfecting the tTA-gene. The cells can be transfected with pUHD15-1 together with a dominant selectable marker gene such as neo[R]. This transfection and subsequent selection and culture should be performed in the presence of tetracycline or suitable analog to avoid inadvertent activation of the tetp5 promoters. G418 resistant colonies can be analyzed for rAAV production by transfection with pIG-CFT, removing the tetracycline and infecting the cells with adenovirus. The rAAV produced can be quantified by RCA. Regulated expression of rep, cap and Large-T-antigen will be verified on Western blot.

Materials and Methods

Constructs: ptetp5repcap was made by cloning a 4.3 kb XbaI fragment derived from pAAV/Ad[7] (a kind gift from Dr. R. J. Samulski) containing the entire rep and cap coding domain in the XbaI site immediately downstream of the tet(o) (FIG. 2). In ptetp5repcap, the tet(o) is situated upstream of a −68 bp p5-promoter (measured from the first base of the TATA-Box). To completely substitute the p5-promoter for the tet(o) we performed a PCR reaction. The upstream primer was 5'-ATTAATCTAGACTAGTCGCGCAGCCGCCATGCCG GGG-3' (SEQ ID NO:1) and the downstream primer was 5'-TGTGGAAGTAGCTCTCTCCC-3' (SEQ ID NO 2). The PCR reaction was performed on pAAV/Ad with pfU™ (Stratagene) using the buffer and the reaction conditions recommended by the manufacturer. The final construct, ptetrepcap, was generated by digesting the 299 bp PCR product with XbaI and SfiI and ligating the resulting 248 bp fragment in a three part ligation with a 3.95 kb SfiI-XbaI fragment from pAAV/Ad into the XbaI site immediately downstream of the tet(o) construct. The amplified part of the construct was sequenced and found to be as anticipated.

The ptetcap construct was derived from construct ptetrepcap by deletion of a large part of the rep-gene and the p40 promoter (self-ligation of a 6.9 kb blunted SpeI and HindIII fragment). ptetp4ocap was derived from construct ptetrepcap by deletion of a large part of the rep-gene but leaving a 220 bp p40 promoter fragment (self-ligation of a 7.2 kb blunted SpeI and BstB1 fragment). pMLPicap was made by ligating the cap-gene (HindIII-BamHI fragment from ptetrepcap) into the HindIII-BamHI site of pMLPiTK. pITRp5p40cap was generated by deleting the SfiI-BstBI fragment of the rep-gene from pSM620 (a molecular clone of AAV in pBR322). ptetrep was generated as follows. The 3' part of the rep-gene was amplified with two specific primers which also carried additional sequences for the restriction enzymes ClaI and AvrII (upstream primer) and BglII and SpeI (downstream primer). The sequence of the upstream primer was 5'-GGTATCGATCCTAGGCGTCAGACGCGGAAGCTTC G-3' (SEQ ID NO 3) and the sequence of the downstream primer was 5'-CCAACTAGTAGATCTGCTTCCACCACTGTCTTATT C-3' (SEQ ID NO 4). The PCR reaction was performed on pAAV/Ad with pfu™0 (Stratagene) using the buffer and the reaction conditions recommended by the manufacturer. The amplified product was digested with ClaI and SpeI and cloned into the ClaI, SpeI site of pBluescript SK[+] to form pBluePCRREP1. The construct was verified by sequencing and found to be as anticipated. The 1.9 kb SpeI-SwaI fragment from ptetrepcap was ligated into the AvrII-SwaI sites from pBluePCRREP1 to form pBlueREP1. pBluetetREP was generated by inserting the ClaI-HindIII fragment from ptetrepcap into the ClaI-HindIII sites of pBlueREP1. ptetrep was generated by ligating the BamHI-BglII SV40 polyadenylation site fragment from pMLPiTK into the BglII site of pBlueREP1.

HtTA cells[52], 293 cells[56] and CV1 cells[60] were maintained in Dulbecco's modified Eagles Medium (DMEM, Life Technologies, Breda, The Netherlands) supplemented by 10% heat inactivated Fetal Bovine Serum (GIBCO, Life Technologies, Breda, The Netherlands, FCS) and 50 ug/ml Gentamycin (GIBCO, Life Technologies, Breda, The Netherlands). The cells were cultured in 10% CO2, 100% humidity at 37° C.

Monoclonal Antibodies: The MOAB 7B7.32 specific for respectively. Rep78, Rep68 was a kind gift of R. Samulski. The MoAB B1 specific for the capsid proteins VP1, VP2 and VP3[61] was a kind gift of J. A. Kleinschmidt.

Protein extraction was performed as described in Kyostio et al[62]. SDS-PAGE gel electrophoresis and Western blotting were performed as described in[63]. MOAB detection of AAV proteins was performed as described below. Nitrocellulose filters were incubated overnight (4° C.) in 5% low fat milk powder. The next day, the filters were washed with wash buffer (PBS containing 0.05% (v/v) TWEEN20). Subsequently, the filters were incubated (1.5 hrs, room temperature) with an appropriate dilution of the monoclonal antibody (MoAB) in wash buffer supplemented with 0.1% (w/v) BSA. The filters were washed 3 times with wash buffer. Rep and Cap proteins were visualized by peroxidase-coupled secondary antibodies and enhanced chemiluminescence detection (ECL kit; Amersham International, Den Bosch, The Netherlands) as described by the supplier.

Hirt-extractions and replication center assays and crude rAAV-isolations were performed as described in[31]. Standard molecular biology techniques, such as Northern blot analysis, cloning and filter hybridization were performed as described in[63].

Transfection of cell lines. DNA transfections were carried out using CaPO4 precipitation kit (Life Technologies, Breda, The Netherlands) according to the manufacturer's specifications.

For the analysis of transient transfection, the cells were harvested after 48 hours. For stable transfections, the cells were co-transfected with the plasmid of interest and plasmid pX343, a hygromycin construct expressing the hygromycin phosphotransferase (hph) gene for resistance to hygromycin B[64]. Stable cell pools carrying the plasmid of interest were generated by selecting the cells for 10–14 days in normal medium supplemented with 400 ug/ml Hygromycin B (Calbiochem, La Jolla, California, U.S.A), with or without tetracycline (2 ug/ml, Sigma, St Louis, U.S.A.) or doxycycline (1 ug/ml, Sigma, St Louis, U.S.A.). This selection medium was replaced twice a week.

Constructs

Construction of Rep-Expression Cassettes

To obtain the final construct ptetp5repEcoNI, the following strategy was employed. First, the TATA-box from plasmid pUHD10-3 was removed to give plasmid pUHD(10-3) ΔKpnI. To this end, the plasmid pUHD 10-3 of 3.15 kb (a kind gift from prof. H Bujard), containing the eptamerized tet-operators upstream of the minimal hCMV promoter (52), was digested with KpnI and self-ligated. Plasmid ptetMCS (3.0 kb) was made by introducing a multiple cloning site (MCS) into XbaI-KpnI digested pUHD(10-3)ΔKpnI. This was done by inserting a phosphorylated double stranded oligo carrying the restriction sites SfiI, BglI, XbaI, EcoNI and AflII with SpeI and KpnI overhanging 5' and 3' ends, respectively. The linker was obtained by hybridizing a sense oligo with sequence 5'-CGGCCGCCTCGGCCCTCTAGAGCCTTCTTAAGGC GA-3' (SEQ ID NO 5) to the anti-sense oligo 5'-CTAGTCGCCTTAAGAAGGCTCTAGAGGGCCGAG GCGGCCGGTAC-3' (SEQ ID NO 6). ptetp5repEcoNI (5.4 kb) was then generated by inserting a 2.4 kb XbaI-EcoNI fragment derived from pSub201 (7) containing the entire Rep gene into XbaI, EcoNI digested ptetMCS.

We next generated a rep-expression plasmid, ptet*p5repEcoNI, with an altered −60 YY1 and Rep-binding site. Two PCR reactions were carried out resulting in a 100 bp p5 promoter fragment and a 630 bp fragment containing the upstream part of the rep. Into these fragments, the specific mutations were inserted through the primers. The 100 bp fragment was amplified with two specific primers, which also included additional sequences for the restriction enzyme sites KpnI, XbaI and SfiI (upstream primer) and KpnI, SpeI and SphI (downstream primer).The sequences of the upstream and downstream primers were respectively: 5'-GGGGTACCTCTAGAGTCCTGTATTAGAGGTCACG TG-3' (SEQ ID NO 7) (pr1) and 5'-CCGGTACCACTAGTACGCATGCTTAAATACCCAG CGTGACCAC-3' (SEQ ID NO 8) (pr2). The reaction was performed on ptetp5repEcoNI with the Expand Long Template PCR System (GIBCO BRL) using buffer and conditions recommended by the manufacturer. The PCR reaction to amplify the upstream part of the rep-gene was carried out by using the upstream primer 5'-GGGGTACCGCATGCGTACTAGTCGAGGGTCTCCA TTTTGAAGCGG-3' (SEQ ID NO 9) (pr3) that also carried additional restriction enzyme sites for KpnI, SphI and SpeI and the rep-specific downstream primer 5'-AACCGTTTACGCTCCGTGAG-3' (SEQ ID NO 10) (pr4). The reaction was performed on ptetp5repEcoNI with pfu DNA polymerase (Stratagene), according to the conditions recommended by the manufacturer. The PCR products contained a 40 bp overlap and were linked by annealing PCR using pfu DNA polymerase, according to the manufacturer's protocol. Approximately 50 ng of each PCR product was used as template for the annealing PCR reaction using primers pr1 and pr4. The resulting 730 bp amplified product was digested with XbaI and NcoI and cloned into XbaI-NcoI digested ptetp5repEcoNI to give ptet*p5repEcoNI. The cloning junctions and the parts derived from PCR from plasmids ptetp5repEcoNI and ptet*p5repEcoNI, were sequenced and found to be as expected.

Construction of Enlarged Cap-Expression Cassettes

The replicated cap-gene in construct pITRp5p40cap is 3.5 kb and can be packaged into AAV-capsids. To avoid this, we enlarged the replicated fragment such that it would be too large to be encapsidated. Due to the absence of suitable restriction sites, we had to redesign the ITRcap construct. An additional objective was to remove the p5-promoter from the ITRcap construct to avoid unnecessary homology between the rep- and the cap-expression cassettes. The resulting construct pITR6.5cap contains between ITRs consecutively, a 538 bp fragment of the human ADA cDNA sequences, p40cap-sequences (nucl. 1624 until 4491 from AAV-2, accession number M12469 Genbank), and sequences 20901–23930 from human ADA intron2 (accession number M13792, Genbank). First, we cloned a PCR-fragment from the human ADA cDNA into NotI-site of pBluescript SK+ to give pBLada. The sequence of the upstream and downstream primer was respectively 5'-ATAAGAATGCGGCCGCTCGCCCTCCCAGCTAACA CA-3' (SEQ ID NO 11) and 5'-AGTTTAGCGGCCGCAGATCTTCGTTCGAAGGCCT GGACATGTCCAGGC-3' (SEQ ID NO 12). The PCR reaction was performed on pAMGI (EMBO J. Vol. 4, pp 437, 1985) with EXPAND long template PCR system (GIBCO BRL), according to the conditions recommended by the manufacturer. The amplified product (538 bp) was digested with NotI and cloned into the NotI site of pBluescript SK+ to form pBLada. To clone the cap-gene in pBLada, we first introduced a phophorylated double stranded NotI-BglII linker with NcoI site nucleotide overhang into the NcoI site, 3' of the cap-coding region in pITRp5p40cap to give pITRp5p40cap+linker. The sequences of the strand and anti-strand oligos were: 5'-CATGGCGGCCGCAGATCTC-3' (SEQ ID NO 13) and 5'-CATGGAGATCTGCGGCCGC-3' (SEQ ID NO 14). To introduce the p40cap sequences in pBLada, we performed a three part ligation. pBLadacap was generated by ligating a 780 bp BstBI-SstII cap fragment from pSM620 (a molecular clone of AAV in pBR322, kind gift from K. I. Berns) and a 2.0 kb SstII-BglII fragment from pITRp5p40cap+linker into BstBI-BglII digested pBLada. Next, we generated an ITR-construct containing the 3.0 kb fragment derived from the second intron of human ADA. The 3.0 kb fragment was derived by PCR from HtTA genomic DNA using the upstream primer 5'-GGACAGATCTGCGGCCGCACTCCTTTAAGTGCGT TACC-3' (SEQ ID NO 15) and the downstream primer 5'-GGAACAGATCTGCGATTCTCCTAATGGTCTCC-3' (SEQ ID NO 16). For cloning purposes, a BglII and a NotI site were introduced in the upstream primer, whereas in the downstream primer, a BglII site was introduced. The PCR reaction was performed with expand long template PCR system (GIBCO BRL) using buffer and reaction conditions recommended by the manufacturer. The PCR fragment was digested with BglII and ligated into BglII digested pTR+ plasmid to yield pTRintronADA (described in Proc Natl Acad Sci U.S.A. Vol. 94, pp 6916–6921, 1997). Next, the final construct pITR6.5cap was generated by ligating a 3.2 kb NotI-fragment from pBLadacap into NotI digested pTRintronADA. Both orientations of the adacap-fragment into pTRintronADA were obtained. In pITR6.5cap, the direction of transcription of the cap-gene is toward the ADA intron-sequence.

The pITR6.5capZEO construct was generated by ligating the 1.2 kb ClaI-XbaI CMV-ZEO fragment from pZEOSV2 into ClaI-NheI digested pITR6.5cap.

The test recombinant AAV plasmid pTR-Luc was generated by amplifying a 3 kb fragment containing the CMV-Luciferase expression cassette from IG-Ad CMV Luc template, described in patent application EP 95202213, with primers 5'-CACAGATCTGCGGCCGCCAGGGGCTGCAGGTCG TTAC-3' (SEQ ID NO 17) and 5'-TGGAGATCTGCGGCCGCCCGCCACACTCGCAGG GTCTG-3' (SEQ ID NO 18) using expand long template PCR system (GIBCO, Life Technologies, Breda, The Netherlands), according to the specifications of the manufacturer. Introduced into the primers were BglII-sites with which the fragment was cloned into the BglII site of pTR+.

Miscellaneous plasmids: pPur and pTK-hyg were obtained from Clontech, Palo Alto, CA USA. pZeoSV2 was obtained from Invitrogen, San Diego, CA USA.

Probes: The Cap-specific probe is a 1,3 bp SstII-NcoI fragment from ptetp40cap. The Luciferase specific probe is a 2 kb BglII-HindIII fragment from pTR-Luc. The ADA-specific probe is a 500 bp NotI-fragment from pBLada. The rep-specific probe is a 650 bp SstI-fragment from ptetp5repEcoNI.

Monoclonal antibodies: MoAB-B1 (αVP) specific for the capsid proteins VP1, VP2 and VP3 (Progen, Heidelberg, Germany). MoAB 303.9 specific for the Rep proteins Rep 78, Rep 68, Rep 52 and Rep 40 (Progen, Heidelberg, Germany).

Mass Screening of Rep-expressing clones using a protein Dot blot assay. Samples to be analyzed by dot blot assay were obtained by lysing the cells from a 6 well dish in 200 microliter protein lysisbuffer (62). Samples were sonicated on ice for 15 seconds on setting 5 (SONIPREP™ 150 (MSE), Beun de Ronde B. V. Abcoude, The Netherlands). Protein content was quantified using the Dc protein assay kit from Biorad (Veenendaal, The Netherlands). 30 and 3 microgram of protein was diluted in blotbuffer (63) devoid of SDS and spotted on IMMUNOBILONP™ transfer membranes (Millipore Corporation, Bedford, Massachusetts, U.S.A.), using a BIO-DOT™ Microfiltration Apparatus from Biorad (Veenendaal, The Netherlands), according to the specifications of the manufacturer. After spotting, the filters were incubated and processed as normal Western blot filters.

Induction of Rep-expression in stable cell lines. To induce rep-expression in cells growing in the presence of doxycycline (1 microgram/ml), the doxycycline needs to be washed away extensively. To this end, cells were washed by replacing the medium four times with fresh culture medium without doxycycline. Subsequently, the cells were infected with adenovirus ts149 at an moi of 20. Unless otherwise stated before, to harvest the cells, the cells were incubated for 24 hours for Hirt-extraction, for 48 hours for protein extraction and for 72 hours for rAAV-isolation.

Titration of pTR-Luc recombinant AAV. Recombinant AAV was produced by transfection (CaPO4 transfection kit, Life Technologies, Breda, The Netherlands) of pTR-Luc on washed and adenovirus infected CARE.1 cells or B1 cells according to the specifications of the manufacturer. After three days, rAAV preparations were made according to the protocol described in (31). To test for the presence of recombinant AAV containing the Luciferase gene, virus was titrated on HtTA cells or adenovirus infected HtTA cells. After 24 hours, the cells were harvested and analyzed for Luciferase activity using the reporter lysis buffer and Luciferase detection kit from Promega (Leiden, The Netherlands) using the protocols supplied by the manufacturer. Detection of Luciferase was performed in a LUMATLB9507™ luminometer (EG and G, Berthold AG, Germany).

Example 7

Generation of a General Packaging Cell Line for rAAV-Vectors

To generate a general packaging cell line for rAAV-vectors, we first generated a new series of rep-expression constructs. One objective was to reduce the amount of cap-specific sequences from the cassette to minimize the possibility of recombination between rep and cap expression constructs that could lead to the formation of replication competent AAV. The other objective was to dissect the promoter driving rep-expressior to further delineate and optimize the cis-acting elements responsible for inducible expression of rep.

Construct ptetp5repEcoNI was different from ptetp5repcap in that we removed the TATA-box originating from the tet-operon and in that sequences 3' of the EcoNI site were deleted to minimize overlap with cap-constructs while retaining all information required for optimal splicing of the rep-specific mRNA (see materials and methods for details). Construct ptet*p5repEcoNI differs from ptetp5repEcoNI in that the rep-binding element in the p5-promoter was replaced by a synthetic linker and that the YY1 site at −60 was deleted (measured from the transcription start site in the p5-promoter).

Figure 13:
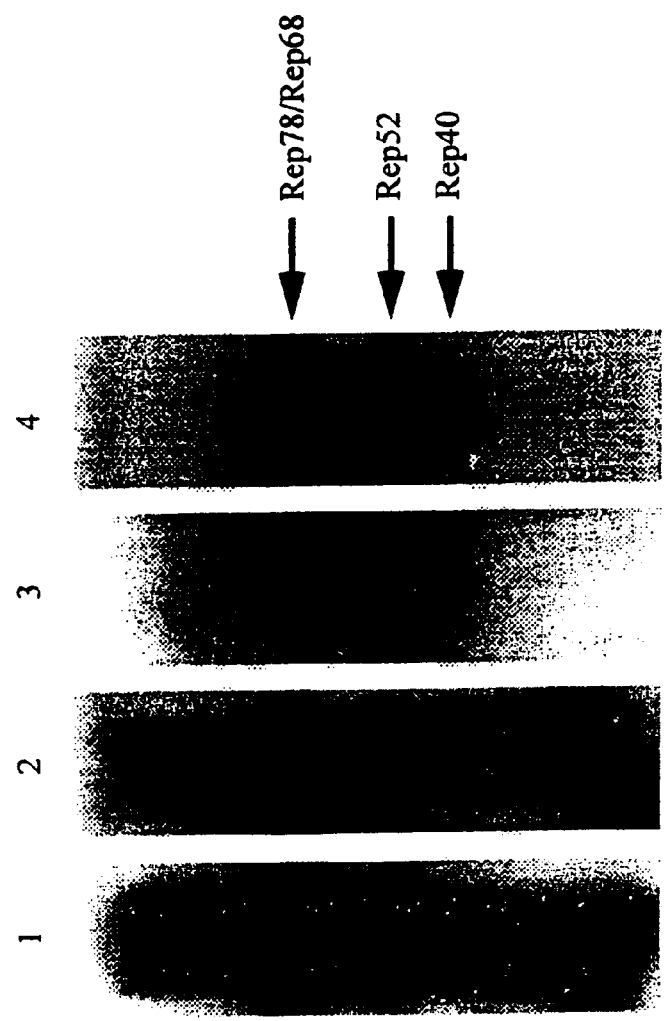
FIG. 13 depicts a Rep-gene expression two days after transfection of plasmid ptetrep (lane 1), ptetp5repcap (lane 2), ptetp5repEcoNI (lane 3) and ptet*p5repEcoNI (lane 4) into adenovirus infected HtTA cells. Shown is an immunoblot with an anti-rep antibody 303.9, a kind gift of Dr. J. Kleinschmidt. Indicated are the locations of Rep78, Rep68, Rep52 and Rep40.

Integrity of the constructs was analyzed in transient expression in adenovirus infected HtTA cells. Protein was harvested after 48 hours and Western blotted (FIG. 13). All constructs expressed rep. In construct ptetrep, only rep-proteins derived from the unspliced messengers are clearly detected, Rep78 and Rep52. In construct ptetp5repEcoNI and ptet*p5repEcoNI, products from the spliced messengers, Rep68 and Rep40, are also detected. Strikingly, in cells transfected with construct ptetp5repEcoNI, Rep52 is by far the most abundant protein. The significance of this is as yet not known. As discussed later, in stable transfected cells this striking abundance of Rep52 was not observed.

Figure 14:
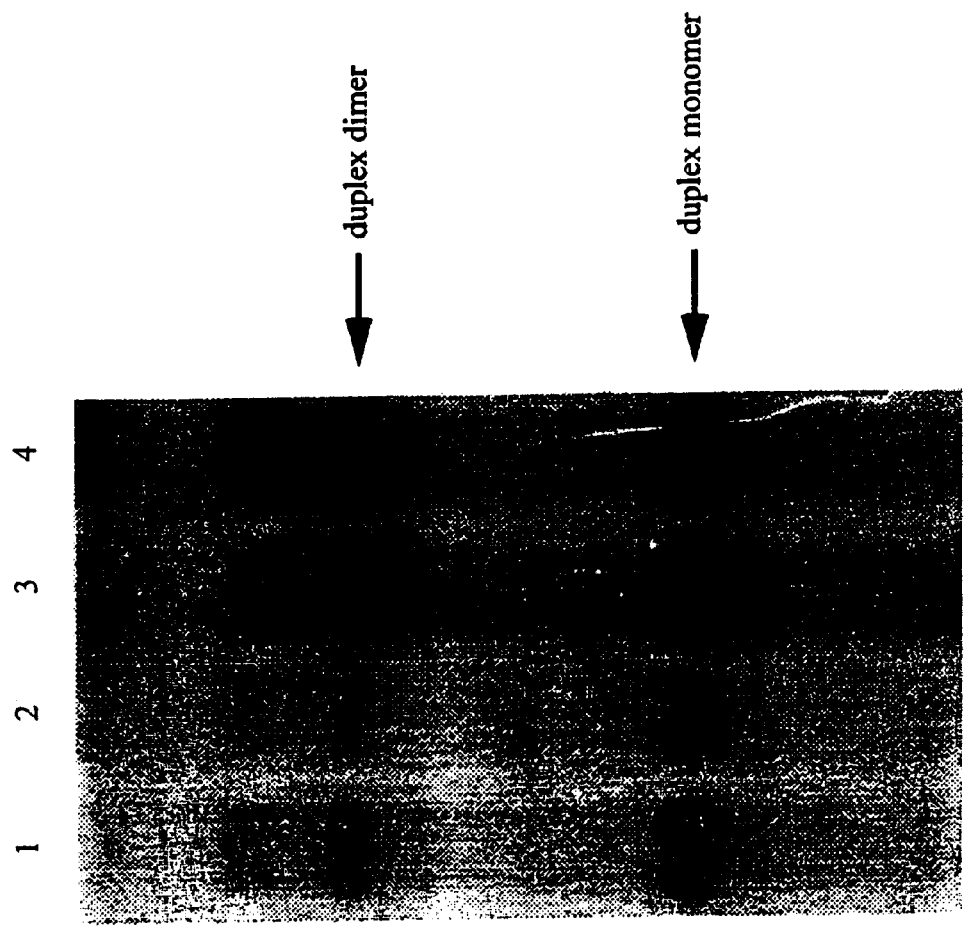
FIG. 14 depicts a Hirt-extract DNA from HtTA cells infected with rAAV produced by HtTA-cap2 cells. Adenovirus infected HtTA cells were transfected with ptetrep and infected with rAAV produced on HtTA-cap2 cells transfected with ptet*p5repEcoNI (lane 1), ptetp5repEcoNI (lane 2), ptetp5repcap (lane 3) or ptetrep (lane 4). Hirt-extract was isolated 24 hours after transfection and infection. The extract was digested with DpnI, Southern blotted and hybridized with a cap-specific probe that contains no sequence overlap with ptetrep. Indicated are the duplex monomer and the duplex dimer of the cap-gene containing rAAV rescued, replicated and packaged in the transfected HtTA-cap2 cells.

To verify whether the rep was functional, we transfected the constructs into adenovirus infected HtTA-cap2 cells and two days later harvested rAAV. HtTA-cap2 cells contain a rescuable 3.5 kb rAAV containing the capsid gene. Functional expression of Rep in these cells leads to rescue, replication and packaging of the cap-construct (described in example 4). For detection of the production of rAAV, the virus preparation was infected on adenovirus infected and ptetrep transfected HtTA cells. After 24 hours, cells were harvested and extrachromosomal DNA was isolated, Southern blotted and probed with a cap-specific probe. In spite off differences in the ratios with which the different Rep-proteins are expressed, all rep-constructs were able to complement the cap-construct in HtTA-cap2 cells (FIG. 14).

Next, we set out to generate cell lines stably transformed with the rep-expression cassette. The constructs were transfected into HtTA cells together with pTK-Hyg. After two weeks of selection with Hygromycin B in the presence of doxycycline, resistant colonies became apparent. Per construct, between 30 and 180 colonies were picked and propagated in 96 well dishes in the absence of selection but in the presence of doxycycline. Confluent wells were trypsinized and 10% was seeded in a fresh 96 well dish and incubated at 32 degrees Celsius to slow down growth. The remainder was seeded in 6 well dishes to test for rep-expression. When the cells in the 6 well dishes reached a confluence of approximately 70%, rep-expression was induced by washing away the doxycycline and the addition of adenovirus. After 48 hours, protein was extracted from the cells and analyzed for Rep-expression.

Figure 15:
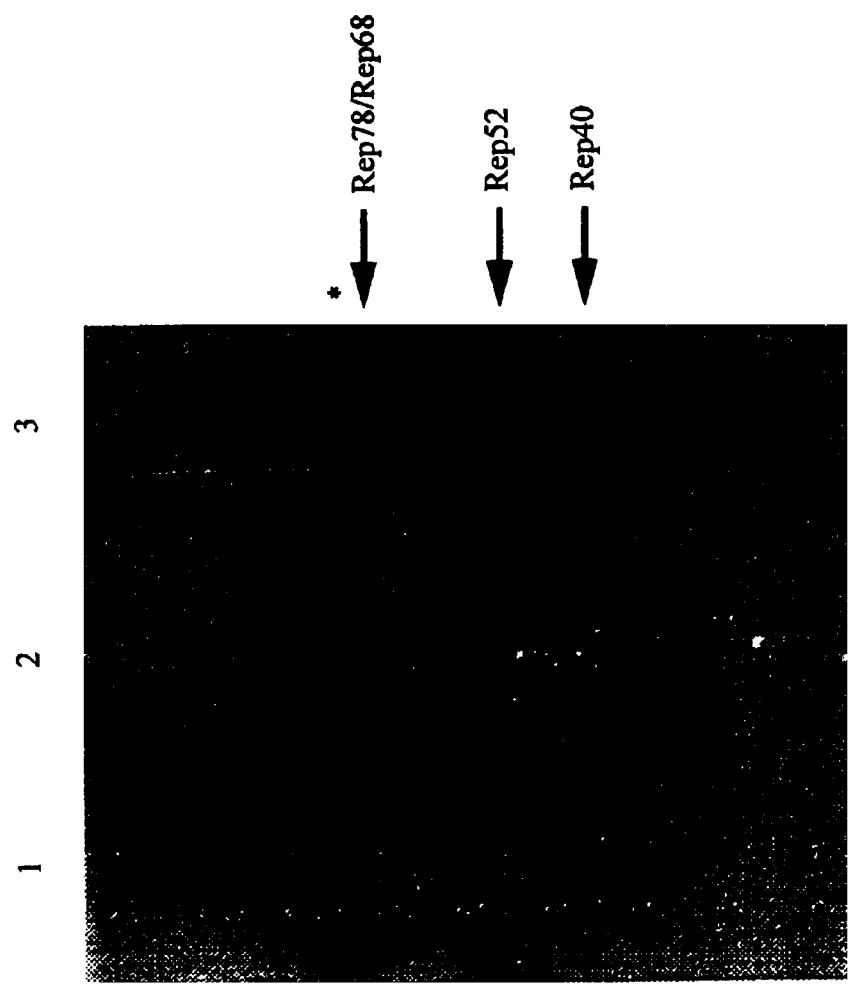
FIG. 15 depicts an expression of Rep proteins in transfected and Hygromycin B selected HtTA-cells. HtTA cells were transfected in the presence of doxycycline with a mixture of pTK-Hyg (Clontech, Palo Alto) and rep-expression plasmids ptetrep (lane 2) or ptetp5repEcoNI (lane 3) Between 30 (ptetrep) and 90 (ptetp5repEcoNI) Hygromycin B resistant colonies were picked and split in two dishes. The cells from one dish were washed to remove the doxycycline and infected with adenovirus. Protein was isolated after 48 hours and equal amounts of protein from six independent colonies were pooled and analyzed for the expression of rep-proteins by Western blot. Rep-proteins were visualized with the antibody 303.9. The positions of Rep78, Rep68, Rep52 and Rep40are indicated. Protein from ptetp5repcap transfected and adenovirus infected HtTA cells served as a positive control (lane 1). A cross-reacting a-specific band is detected with this batch of antibody (*)
Figure 16:
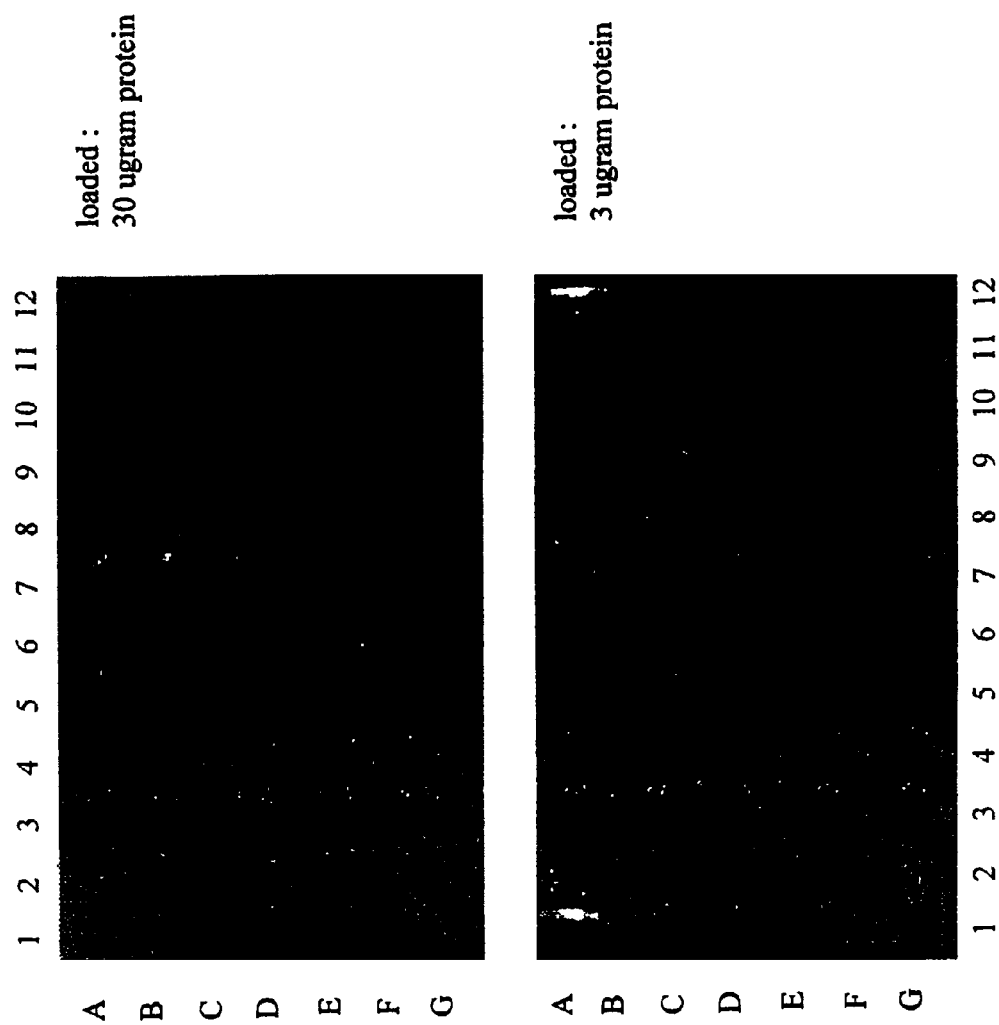
FIG. 16 depicts a Western dot blot assay. HtTA cells were transfected in the presence of doxycycline with a mixture of pTK-Hyg (Clontech, Palo Alto) and rep-expression plasmids ptet*p5repEcoNI or plasmid ptetp5repcap. Colonies from only pTK-Hyg transfected HtTA cells served as a negative control. Hygromycin B resistant clones were picked and cells from each clone were divided over two dishes. One dish was used to continue culture of cells for future reference while the cells from the other dish were used to analyze Rep-protein expression. To induce Rep-expression, the cells were washed to remove the doxycycline and infected with adenovirus. Protein was isolated after 48 hours and 30 or 3 microgram of protein was spotted on nitrocellulose filters. Rep-proteins were visualized with antibody 303.9. Protein from 52 colonies from ptet*p5repEcoNI/pTK-Hyg transfected HtTA cells (A1–A12; B1–B12; C1–C12; D1–D12 and E1–E4). Protein from 24 colonies from ptetp5repcap/ pTK-Hyg transfected HTTA cells (E6–E12, F1–F12, G1–G5). Protein from 5 colonies from pTK-Hyg transfected HtTA cells (E5, G6–G9). At location G10, protein from a transient transfection of ptet*p5repEcoNI in adenovirus infected HtTA-cells was spotted. Arrows indicate protein samples of clones reacting with the antibody 303.9.
Figure 17:
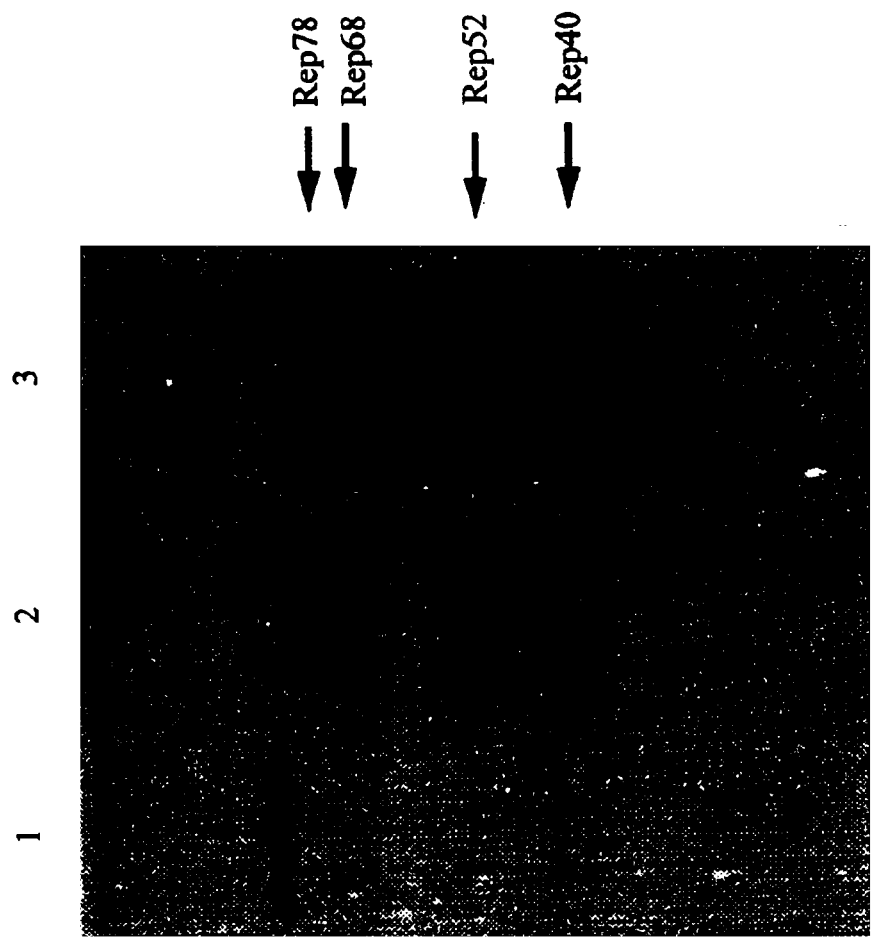
FIG. 17 shows a Rep-expression in HtTA cells stably transfected with ptetp5repcap or ptetp5repEcoNI. HtTA-rep1 (lane 2) and HtTA-rep2 (lane 3) cells were washed to remove the doxycycline and infected with adenovirus. Protein was harvested after 48 hours and Western blotted. Rep-proteins were visualized with the antibody 303.9. Protein from adenovirus infected HtTA cells served as a negative control (lane 1). A cross-reacting a-specific band is detected with this batch of antibody (*).
Figure 18:
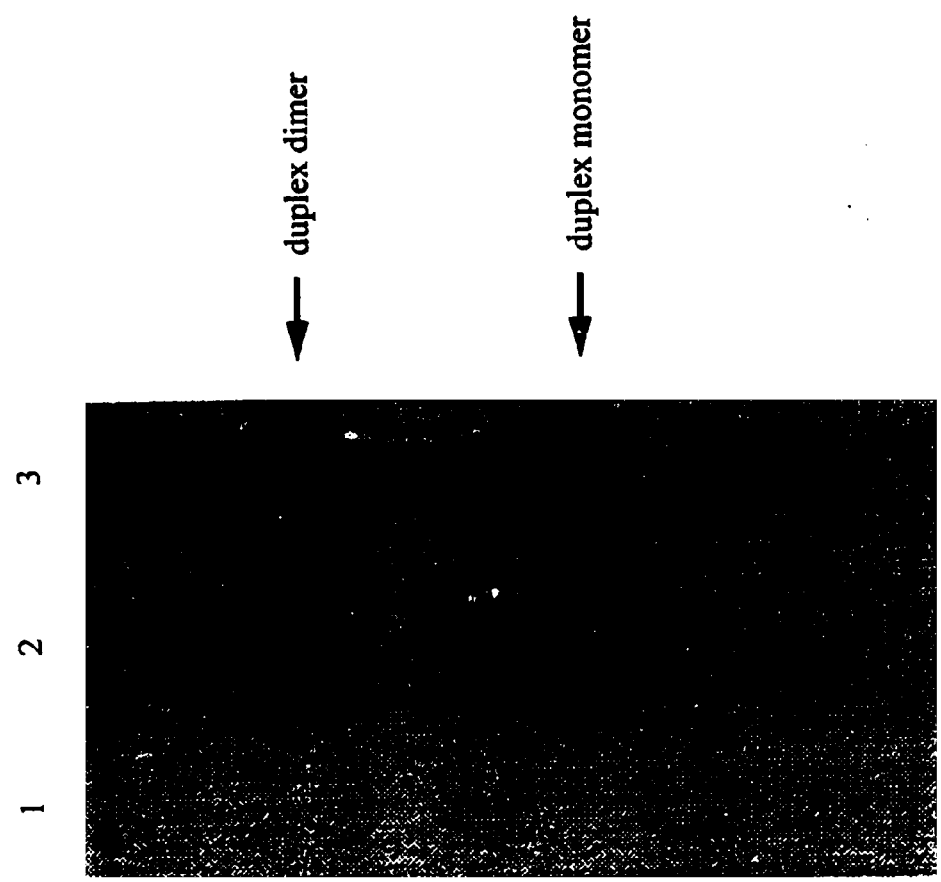
FIG. 18 shows the rescue and replication of rAAV in HtTA-rep1 (lane 2) and HtTA-rep2 (lane 3) cells. HtTA-rep1 and HtTA-rep2 cells were washed to remove the doxycycline, infected with adenovirus and transfected with rAAV plasmid pTR-Luc. After 36 hours, extrachromosomal DNA was isolated by Hirt-extraction and digested with DpnI. The DNA was electrophoresed and Southern blotted. Recombinant AAV specific DNA was visualized with a Luc specific probe. Indicated are the duplex monomer and the duplex dimer replication products. Hirt-extract DNA from adenovirus infected HtTA cells served as a negative control (lane 1).

To get an indication for the presence of clones with the capacity to express Rep-proteins, we pooled the proteins from 6 clones derived from the transfection with construct ptetrep and from the transfection with ptetp5repEcoNI. As expected, with the tet-operon construct ptetrep construct, no Rep-expression was detectable, whereas in the pool derived from the tet-operon+p5 promoter construct, ptetp5repEcoNI, rep-expression was readily detectable (FIG. 15). To mass screen all the colonies obtained from the transfection, we performed a Western dot blot assay in which a dilution titration of 30 and 3 microgram of protein of each clone was spotted on a filter. Rep-proteins were visualized with the antibody 303.9 detecting all four Rep-proteins. An example of this assay is given in FIG. 16. The arrows indicate protein samples staining with the antibody also in the lowest concentration of protein. These samples were further analyzed on a normal Western blot. Clones which gave the highest Rep-expression were expanded and stored for future reference. One ptetp5repcap and one ptetp5repEcoNI derived clone, designated HtTA-rep1 and HtTA-rep2 respectively, were studied in more detail. Neither the large number of clones arising with the different clones nor the subsequent unaltered growth speed of the colonies and the two selected clones indicated a large toxic or growth inhibiting effect of carrying the rep-expression construct. Thus, we expected the clones to be, at least, fairly stable and would not lose the rep-expression cassette upon continued culture. To verify this assumption, we cultured the clones for 26 passages without selection, but in the presence of doxycycline, and analyzed them first for rep-expression on Western blot. To induce rep-expression, the cells were washed extensively to remove the doxycycline and infected with adenovirus. After 48 hours, protein was extracted and Western blotted. Both HtTA-rep1 and HtTA-rep2 expressed rep after induction (FIG. 17). Interestingly, HtTA-rep1 expresses all four Rep-proteins, whereas in HtTA-rep2, Rep78 is not detectable. To verify whether the rep-gene in the cells was functional, we analyzed whether recombinant AAV constructs were able to replicate in these clones. To this end, the cells were washed to remove the doxycycline and infected with adenovirus. Simultaneously, the cells were transfected with a plasmid containing the pTR-Luc vector (FIG. 18). After 24 hours, the cells were harvested and extra-chromosomal DNA was isolated, digested with DpnI, Southern blotted and probed with a Luciferase specific probe. Clearly detectable are DpnI resistant extra-chromosomal bands corresponding in size to the duplex monomer and the duplex dimer of the replicated pTR-Luc vector. From these experiments, we conclude that the expression cassettes in HtTA-rep1 and the HtTA-rep2 are functional. Considering the fact that the cells were only selected with Hygromycin B for two weeks following transfection and were cultured and expanded without selection for more then 3 months, we conclude that the clones are stable and that there is no strong selection against the presence of the rep-expression cassette in these clones.

Figure 19:
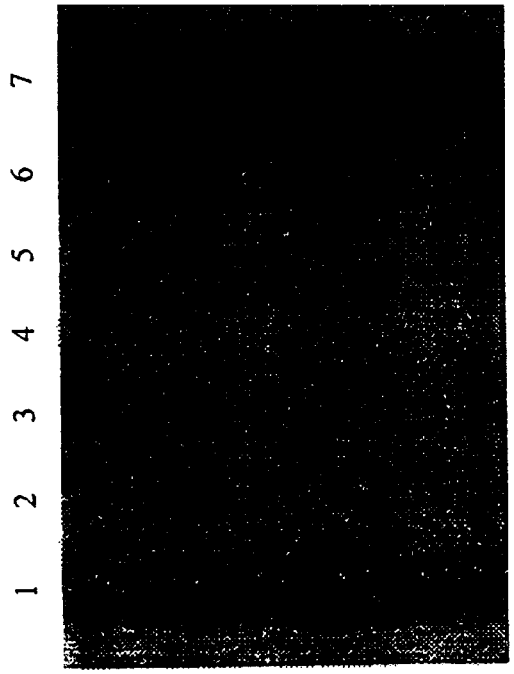
FIG. 19 shows the rescue and replication of pITR6.5cap in adenovirus infected CARE.1 cells. CARE.1 cells were seeded in medium without doxycyline and either infected (lane 7) or not infected (lane 6) with adenovirus. After 36 hours, extrachromosomal DNA was isolated, run on agarose and Southern blotted. In panel A is depicted a 10 minute exposure of a Southern blot hybridized with a cap-specific probe. Puromycin resistant HtTA-rep1 cells derived from clone B1 infected (lane 5) or not infected (lane 4) served as negative controls. In lane 1 is loaded Hirt-extract DNA of a transient transfection of pITR6.5cap and ptet*p5repEcoNI into adenovirus infected HtTA cells. Lane 2 and lane 3 contain Hirt-extract DNA from adenovirus infected HtTA cells and adenovirus infected HtTA-rep1 cells, respectively.
Figure 19:

In HtTA-rep1, also, the cap-gene is stably integrated into the host cell genome. Although Western blot analysis revealed expression of all Rep-proteins, capsid gene expression was often undetectable and, in the best experiments, very low (not shown). To generate a general packaging cell line expressing both the rep- and the cap-gene, we introduced into HtTA-rep1 and HtTA-rep2 cells a construct, pITR6.5cap, in which the cap-gene is flanked by two AAV-TR. To prevent packaging of this rAAV-molecule, the total size of the rAAV was enlarged to 6.5 kb by introducing sequences from the human Adenosine Deaminase (hADA) gene. HtTA-rep1 and HtTA-rep2 cells were co-transfected with construct pITR6.5cap and pPur, a plasmid expressing the dominant selectable marker gene puromycin. After transfection and a two week selection in puromycin (2.5 microgram/ml), individual puromycin resistant colonies were picked and expanded in the absence of puromycin. To select clones stably transformed with at least one intact copy of the AAV-cap construct, cells from individual colonies were seeded in 6 well dishes in the absence of doxycycline and infected with adenovirus. After 36 hours, the cells were harvested and extrachromosomal DNA was isolated, Southern blotted and probed with a hADA specific probe. One clone out of the 14 colonies tested, derived from the transfection of HtTA-rep1 cells, produced a detectable amount of excised and extrachromosomaly replicated AAV-cap construct. This clone, designated CARE.1, and a negative clone, B1, were expanded and the replication experiment was repeated (FIG. 19, panel A). As expected, no replicated cap-expression cassette was detected in uninduced CARE.1 cells. Upon induction with adenovirus in the absence of doxycycline, excised and replicated cap-expression cassettes are readily detectable, even on a 10 minute exposure of the Southern blot (FIG. 19, panel A). Neither the negative clone B1, nor the parent HtTA-rep1 or the HtTA cell line contain this fragment. To exclude the possible generation of replication competent AAV, the Hirt-extracts were analyzed with a rep-specific probe (FIG. 19, Panel B). No specific bands of approximately 4.7 kb are detected, even after overnight exposure. There is some signal in the high molecular weight range that corresponds most likely to non-specific hybridization to residual chromosomal and adenovirus DNA. In contrast to the safe integrated state, we detected in the transient transfection of pITR6.5cap and ptet*p5repEcoNI on adenovirus infected HtTA cells a replication competent rAAV carrying rep-gene sequences. The size of this fragment is 3.5 kb for the duplex monomer and approximately 7 kb for the duplex dimer, which is too small for both the rep- and the cap-gene to be present intact on this recombination product. We next tested the expression of rep- and cap-gene products in CARE.1 cells. Uninduced CARE.1 cells do not express rep or cap-gene products (FIG. 20). Upon infection with adenovirus in the absence of doxycycline, Rep78, Rep68 and a small amount of Rep52 are detected. Readily detected are also VP1, VP2 and VP3. Moreover, the relative ratio of the three capsid proteins mimics the relative abundance of the proteins in AAV-capsid and in wtAAV producing cells. As expected, the clone B1, from which no pITR6.Scap is rescued and replicated, expresses upon induction only rep-gene products. The also present cap-expression cassette is not expressed in clone B1, also not upon adenovirus infection. The ptetp5repcap expression cassette is not rescued and replicated by the AAV-rep proteins produced. Normal HtTA cells served as a negative control and, as expected, do not express either Rep or Cap.

Next, we determined virus production by the CARE.1 cells. CARE.1 cells and, as a negative control, B1 cells were washed, infected with adenovirus and transfected with pTR-Luc. After three days, virus was harvested and used to infect normal HtTA cells and adenovirus infected HtTA cells. After 24 hours, Luciferase was measured. In contrast to rAAV produced on B1 cells, rAAV produced on CARE.1 cells produced detectable luciferase activity in target cells and, thus, produced rAAV (Table 1).

LITERATURE

1. Berns K I: Parvovirus replication. Microbiol. Rev. 54:316–329, 1990
2. Berns K I: Parvoviridae and their replication, in Chanock R M, Hirsch M S, Melnick J L, Monath T P, Roizman B (eds): Virology, New York, Raven Press, 1990, p 1743–1763
3. Kotin R M, Siniscalco M, Samulski R J, Zhu X, Hunter L, Laughlin S, Muzyczka N, Rocchi M, Berns K I: Site-specific integration by adeno-associated virus. Proc Natl Acad Sci U.S.A. 87:2211–2215, 1990
4. Samulski R J, Zhu X, Xiao X, Brook J D, Housman D E, Epstein N, Hunter L A: Targeted integration of adeno-associated virus (AAV) into human chromosome 19. EMBO J. 10:3941–3950, 1991
5. Samulski R J: Adeno-associated virus. Integration at a specific chromosomal locus. Curr Opin Gen Dev 3:74–80, 1993
6. Lusby E, Fife K H, Berns K I: Nucleotide sequence of the inverted terminal repetition in adeno-associated virus DNA. J. Virol. 34:402–409, 1980
7. Samulski R J, Chang L, Shenk T: Helper-free stocks of recombinant adeno-associated viruses: normal integration does not require viral gene expression. J. Virol. 63:3822–3828, 1989
8. Ruffing M, Heid H, Kleinschmidt J A: Mutations in the carboxy terminus of adeno-associated virus 2 capsid proteins affect viral infectivity: lack of an RGD integrin-binding motif. J-Gen-Virol 75:3385–92, 1994
9. Srivastava A, Lusby E, Berns K: Nucleotide sequence and organization of the adeno-associated virus 2 genome. J. Virol. 45:555–564, 1983
10. Berns K, Bohensky R: Adeno-associated virus: an update. Adv. Virus Res. 32:243–306, 1987
11. Chejanovsky N, Carter B J: Mutagenesis of an AUG codon in the adeno-associated virus rep gene: effects on viral DNA replication. Virology 173:120–128, 1989
12. Trempe J P, Carter B J: Alternate mRNA splicing is required for synthesis of adeno-associated virus VP1 capsid protein. J of Virol 62:3356–3363, 1988
13. Hermonat P L, Muzyczka N: Use of adeno-associated virus as a mammalian DNA cloning vector: transduction of neomycin resistance into mammalian tissue culture cells. Proc Natl Acad Sci U.S.A. 81:6466–6470, 1984
14. Tratschin J D, Miller I L, Smith M G, Carter B J: Adeno-associated virus vector for high-frequency integration, expression, and rescue of genes in mammalian cells. Mol. Cell. Biol. 5:3251–3260, 1985
15. McLaughlin S K, Collis P, Hermonat P L, Muzyczka N: Adeno-associated virus general transduction vectors: analysis of proviral structures. J. Virol. 62:1963–1973, 1988
16. Muzyczka N: Use of adeno-associated virus as a general transduction vector for mammalian cells. Curr Top Microbiol Immunol 158:97–129, 1992
17. Valerio D: Retrovirus vectors for gene therapy procedures. Transgenic animals 211–246, 1992
18. Morgan R, Anderson W: Human Gene Therapy. Ann Rev Biochem 63:191–217, 1993
19. Holscher C, Horer M, Kleinschmidt J A, Zentgraf H, Burkle A, Heilbronn R: Cell lines inducibly expressing the adeno-associated virus (AAV) rep gene: Requirements for productive replication of rep negative AAV mutants. J of Virol 68:7169–7177, 1994
20. Yang Q, Chen F, Trempe J P: Characterization of cell lines that inducibly express the adeno-associated virus Rep proteins. J of Virol 68:4847–4856, 1994
21. Tratschin J D, Tal J, Carter B J: Negative and positive regulation of gene expression from adeno-associated virus vector in mammalian cells by a viral rep gene product. Mol Cell Biol 6:2884–2894, 1986
22. Heilbronn R, Burkle A, Stephan S, zur Hausen H: The adeno-associated virus rep gene suppresses herpes simplex virus-induced DNA amplificatior. J Virol 64:3012–3018, 1990
23. Trempe J, Carter B: Regulation of adeno-associated virus gene expression in 293 cells: control of mRNA abundance and translation. J Virol 62:68–74, 1988
24. Beaton A, Palumbo P, Berns K: Expression of the AAV p5 and p19 promoters is negatively regulated in trans by the rep protein. J Virol 63:4450–4454, 1989
25. Hermonat P: Down-regulation of the human c-fos and c-myc proto-oncogene promoters by adeno-associated virus Rep78. Cancer Lett 81:129–136, 1994
26. Bantel-Schaal U, zur Hausen H: Adeno-associated viruses inhibit SV40 DNA amplification and replication of herpes simplex virus in SV40-transgormed hamster cells. Virology 164:64–74, 1988
27. Hermonat P: Inhibition of bovine papillomavirus plasmid DNA replication by adeno-associated virus. Virology 189:329–333, 1992
28. Holscher C, Kleinschmidt J, Burkle A: High-level epxression of Adeno-associated virus (AAV) Rep78 or Rep68 protein is sufficient for infectious-particle formation by a rep-negative AAV-mutant. J. Virol. 69:6880–6885, 1995

29. Clark K, Voulgaropoulou F, Fraley D, Johnson P: Cell lines for the production of recombinant adeno-associated virus. Human Gene Ther. 6:1329–1341, 1995
30. Clark K, Voulgaropoulou F, Johnson P: A stable cell line carrying adenovirus-inducible rep and cap genes allows for infectivity titration of adeno-associated virus vectors. Gene Therapy 3:1124–1132, 1996
31. Einerhand M, Antoniou M, Zolotukhin S, Muzyczka N, Berns K, Grosveld F, Valerio D: Regulated high-level b-globin gene expression in erythroid cells following recombinant adeno-associated virus-mediated gene transfer. Gene Ther 2:336–343, 1995
32. Cole C: Polyomavirinae: The viruses and their replication, in Fields B, Knipe D, Howley P (eds): Fields Virology, Philadelphia, Lippencott—Raven Publishers, 1996, p 1997–2025
33. Gluzman Y: SV40 transformed cells support the replication of early SV40 mutants. Cell 23:175–182, 1981
34. Lefebvre R, Riva S, Berns K: Conformation takes precedence over sequence in adeno-associated virus DNA replication. Mol Cell Biol 4:1416–1419, 1984
35. Thomson B, Weindler F, Gray D, Swaab V, Heilbronn R: Human Herpesvirus 6 (HHV-6) is a helpervirus for adeno-associated virus type 2 (AAV-2) and the AAV-2 rep gene homologue in HHV-6 can mediate AAV-2 DNA replication and regulate gene expression. Virology 204:304–311, 1994
36. Hynes N E, Kennedy N, Rahmsdorf U, Groner B: Proc Natl Acad Sci U.S.A. 78:2038–2042, 1981
37. Lee F, Mulligan R, Berg P, Ringold G: Nature 294:228–232, 1981
38. Brinster R L, Chen H Y, Warren R, Sarthy A, Palmiter R D: 296 1982
39. Mayo E K, Warren R, Palmiter R D: Cell 29:99–108, 1982
40. Searle P F, Stuart G W, Palmiter R D: Mol Cell Biol 5:1480–1489, 1985
41. Klock G, Strahle U, Schutz G: Nature 329:734–736, 1987
42. Israel D I, Kaufman R J: Nucleic Acids Res 17:2589–2604, 1989
43. Nouer L: in Nouer L (eds): Heat Shock Response, Boca Raton, Fla., CRC, 1991, p
44. Lee S W, Tsou A-P, Chan H, Thomas J, Petrie K, Eugui E M, Allison A C: Proc Natl Acad Sci 85:1204–1208, 1988
45. Brown M, Figge J, Hansen U, Wright C, Jeang K-T, Khoury G, Livingston D M, Roberts T M: Cell 49:603–612, 1987
46. Hu MC-T, Davidson N: Cell 48:555–566, 1987
47. Figge J, Wright C, Collins C J, Roberts T M, Livingston D M: Cell 52:713–722, 1988
48. Deuschle U, Hipskind R A, Bujard H: Science 248:480–483, 1990
49. Labow M A, Baim S B, Shenk T, Levine A J: Mol Cell Biol 10:3343–3356, 1990
50. Baim S B, Labow M A, Levine A J, Schenk T: Proc Natl Acad Sci U.S.A. 88:5072–5076, 1991
51. Gatz C, Kaiser A, Wendenburg R: Regulation of a modified CaMV 35S promoter by the Tn-10-encoded Tet-repressor in transgenic tobacco. Mol Gen Genet 227:229–237, 1991
52. Gossen M, Bujard H: Tight control of gene expression in mammalian cells by tretracycline-responsive promoters. Proc Natl Acad Sci U.S.A. 89:5547–5551, 1992
53. Gossen M, Fruendlieb S, Bender G, Mueller G, Hillen W, Bujard H: Transcriptional activation by tetracyclines in mammalian cells. Science 268:1766–1769, 1995
54. Chang l-S, Shi Y, Shenk T: Adeno-associated virus p5 promoter contains an adenovirus E1A-inducible element and a binding site for the major late transcription factor. J. Virol 63:3479–3488, 1989
55. McCarty D, Pereira D, Zolotukhin I, Zhou X, Ryan J, Muzyczka N: Identification of linear DNA sequences that specifically bind to the adeno-associated virus rep-protein. J Virol 68:4988–4997, 1994
56. Graham F L, Smiley J, Russell W C, Naiva R: Characteristics of a human cell line transformed by DNA from adenovirus type 5. J. Gen. Virol. 36:59–72, 1977
57. McCarty D M, Christensen M, Muzyczka N: Sequences required for coordinate induction of adeno-associated virus p19 and p40 promoters by Rep protein. J-Virol 65:2936–45 issn: 0022-538x, 1991
58. Ruffing M, Zentgraf H, Kleinschmidt J A: Assembly of viruslike particles by recombinant structural proteins of adeno-associated virus type 2 in insect cells. J-Virol 66:6922–30 issn: 0022-538x, 1992
59. Yang Q, Chen F, Ross J, Trempe J P: Inhibition of cellular and SV40 DNA replication by the adeno-associated virus Rep proteins. Virology 207:246–50 issn: 0042-6822, 1995
60. Jensen F C, al. e: Proc. Natl. Acad. Sci. U.S.A. 53:53, 1964
61. Wistuba A, Weger S, Kern A, Kleinschmidt J: Intermediates of adeno-associated virus type 2 assembly: identification of soluble complexes containing Rep and Cap proteins. J. Virol 69:5311–5319, 1995
62. Kyostio S, Owens R, Weitzman M, Antoni B, Chejanovsky N, Carter B: Analysis of adeno-associated virus (AAV) wild-type and mutant rep-proteins for their abilities negatively regulate AAV p5 and p19 mRNA levels. J. Virol. 68:2947–2957, 1994
63. Maniatis T, Fritsch E F, Sambrook J: Molecular cloning (A laboratory Manual). 1982
64. Sugden B, March K, Yates J: A vector that replicates as a plasmid and can be efficiently selected in B-lymphoblasts transformed by Epstein-Barr virus. Mol Cell Biol 5:410–413, 1985

TABLE 1

| | Luciferase activity in rAAV infected HtTA | | | |
|---|---|---|---|---|
| Dilution of rAAV | rAAV from clone B1 | | rAAV from CARE.1 | |
| | −Ad | +Ad | −Ad | +Ad |
| 2 | 100 | 51 | 2269 | 2656 |
| 50 | 294 | 37 | 226 | 502 |

What is claimed is:

1. A method for producing a nucleic acid which can be conditionally replicated, said nucleic acid not comprising a rep gene, but comprising at least a functional part of a cap gene of Adeno Associated Virus (AAV), which nucleic acid is present integrated in the genome of a eukaryotic host cell, said method comprising providing said nucleic acid with at least one regulatory element which essentially represses replication of said nucleic acid in an integrated setting, but allows replication in an episomal setting, and further providing said nucleic acid with at least a means for functionally excising said nucleic acid in a functional form upon the presence of a signal for excision, thereby producing a nucleic acid which can be conditionally replicated, wherein replication is conditional on said nucleic acid being in an episomal functional form.

2. The method according to claim 1 wherein a means for excision is provided in the form of two AAV-ITR's on either side of the nucleic acid of interest.

3. The method according to claim 1 wherein the signal is at least a functional part of a Rep-protein of AAV.

4. The method according to claim 1 wherein said means for excision is from a viral replication system.

5. The method according to claim 4 wherein the excision means is from a papova virus.

6. The method according to claim 5 wherein the signal is at least a functional part of the large T-antigen.

7. A method for producing a nucleic acid which can be conditionally transcribed which nucleic acid is at least a part of a DNA molecule of interest which DNA molecule does not comprise a rep gene, but comprises at least a functional part of a cap gene of Adeno Associated Virus (AAV) and is present in the genome of a eukaryotic host cell, said method comprising providing said DNA molecule with at least one regulatory element which essentially represses replication of said DNA molecule in an integrated setting, but allows replication in an episomal setting, further providing said DNA molecule with at least a means for functionally excising said DNA molecule in a functional form upon the presence of a signal for excision, thereby producing a nucleic acid which can be conditionaly transcripted, wherein transcription is conditional on said DNA molecule being in an episomal functional form.

8. The method according to claim 7 wherein transcription is under control of an inducible promoter.

9. The method according to claim 7 wherein a means for excision is from a viral replication system.

10. The method according to claim 7 wherein means for excision is provided in the form of two AAV-ITR's on either side of the DNA molecle of interest.

11. The method according to claim 7 wherein the signal is at least a functional part of a Rep-protein of AAV.

12. A method for producing a nucleic acid molecule of interest which can be conditionally expressed which nucleic acid molecule of interest does not comprise a rep gene, but comprises at least a functional part of a cap gene of Adeno Associated Virus (AAV) and is present in the genome of a eukaryotic host cell, said method comprising providing said nucleic acid molecule of interest with at least one regulatory element which essentially represses replication of said nucleic acid of interest in an integrated setting, but allows replication in an episomal setting, further providing said nucleic acid of interest with at least a means for functionally excising said nucleic acid of interest in a functional form upon the presence of a signal for excision, thereby producing a nucleic acid molecule of interest which can be conditionally expressed, wherein expression is conditional on said nucleic acid of interest being in an episomal functional form.

13. The method according to claim 12 wherein transcription is under control of an inducible promoter.

14. The method according to claim 12 wherein means for excision is provided in the form of two AAV-ITR's on either side of the nucleic acid of interest.

15. The method according to claim 12 wherein the signal is at least a functional part of a Rep-protein of AAV.

16. A recombinant vector for carrying out a method for producing a nucleic acid molecule which can be conditionally expressed which nucleic acid molecule does not comprise a rep gene, but comprises at least a functional part of a cap gene of Adeno Associated Virus (AAV) and is present integrated in the genome of a eukaryotic host cell, said recombinant vector comprising a nucleic acid sequence of interest, means for integration into the genome of the eukaryotic host cell, means for functional excision of the nucleic acid sequence of interest after integration upon the presence of a signal for excision, means for essentially repressing replication of said nucleic acid sequence of interest in an integrated setting, and means for allowing replication of the nucleic acid of interest in an episomal setting, wherein one or more of the mentioned means may be one and the same.

17. The recombinant vector of claim 16 further comprising an inducible promoter.

18. The recombinant vector of claim 16 wherein at least one of the mentioned means is from AAV.

19. The recombinant vector of claim 18 comprising at least one of the following elements: a functional part of a cap-gene and an ITR from AAV.

20. The recombinant vector of claim 16 wherein at least one of the elements is from a papovavirus.

21. The recombinant vector of claim 20 comprising an SV40 origin of replication.

22. The recombinant vector of claim 16 further comprising at least a functional part of a rep-gene.

23. The recombinant vector of claim 22 wherein the rep-gene is under control of a combination of two inducible repressor/activator sequences.

24. A recombinant eukaryotic host cell comprising a recombinant vector for carrying out a method for producing a nucleic acid molecule which can be conditionally expressed which nucleic acid molecule does not comprise a rep gene, but comprises at least a functional part of a cap gene of Adeno Associated Virus (AAV) and is present integrated in the genome of a eukaryotic host cell, said recombinant vector comprising a nucleic acid sequence of interest, means for integration into the genome of the eukaryotic host cell, means for functional excision of the nucleic acid sequence of interest after integration upon the presence of a signal for excision, means for essentially repressing replication of said nucleic acid sequence of interest in an integrated setting, and means for allowing replication of the nucleic acid sequence of interest in an episomal setting, wherein one or more of the aforementioned means may be one and the same.

25. The cell of claim 24 further comprising a vector encoding at least a functional part of a rep-gene of AAV.

26. The cell of claim 25 which comprises all AAV genes in trans, wherein said AAV genes were excised from recombinant AAV vector.

* * * * *